United States Patent
Michalakos et al.

(10) Patent No.: US 11,747,311 B2
(45) Date of Patent: *Sep. 5, 2023

(54) HYDROCARBON BYPRODUCT MONITORING OF FIBROUS SUBSTRATES

(71) Applicant: Honeywell International Inc., Charlotte, NC (US)

(72) Inventors: Peter M. Michalakos, Arlington Heights, IL (US); Amanda Childers, Arlington Heights, IL (US); Stephen Yates, South Barrington, IL (US); Sean Skomurski, Highland Park, IL (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/208,933

(22) Filed: Mar. 22, 2021

(65) Prior Publication Data

US 2022/0299484 A1    Sep. 22, 2022

(51) Int. Cl.
*G01N 30/02*    (2006.01)
*C01B 3/34*    (2006.01)
(Continued)

(52) U.S. Cl.
CPC ............. *G01N 30/02* (2013.01); *C01B 3/045* (2013.01); *C01B 3/34* (2013.01); *C01B 3/50* (2013.01);
(Continued)

(58) Field of Classification Search
CPC .. C01B 3/045; C01B 3/34; C01B 3/50; C07C 1/12; C07C 9/04
See application file for complete search history.

(56) References Cited

U.S. PATENT DOCUMENTS

| 7,101,463 B1 | 9/2006 | Weinecke et al. |
| 7,374,731 B2 | 5/2008 | Wang et al. |

(Continued)

FOREIGN PATENT DOCUMENTS

DE    102011014824 A1    9/2012

OTHER PUBLICATIONS

Yates et al., "Hydrogen Recovery by Methane Pyrolysis to Elemental Carbon," 49th International Conference on Environmental Systems, Jul. 7-11, 2019, 16 pp.
(Continued)

*Primary Examiner* — Jafar F Parsa
(74) *Attorney, Agent, or Firm* — Shumaker & Sieffert, P.A.

(57) ABSTRACT

The disclosure describes a system for generating hydrogen gas from a hydrocarbon through pyrolysis with reduced soot formation and increased carbon loading. The system includes one or more pyrolysis reactors configured to generate the hydrogen gas from the hydrocarbon through pyrolysis. Each pyrolysis reactor of the one or more pyrolysis reactors includes one or more fibrous substrates and a concentration sensor downstream of at least one fibrous substrate of the one or more fibrous substrates. Each fibrous substrate of the one or more fibrous substrates defines a deposition surface for carbon generated from the pyrolysis of the hydrocarbon and includes a plurality of fibers configured to maintain chemical and structural stability between 850° C. and 1300° C. The concentration sensor is configured to measure a concentration of at least one of a hydrocarbon byproduct or a hydrocarbon soot precursor, such as acetylene.

20 Claims, 9 Drawing Sheets

(51) Int. Cl.
  *C01B 3/50* (2006.01)
  *C07C 1/12* (2006.01)
  *C01B 3/04* (2006.01)

(52) U.S. Cl.
  CPC .......... *C07C 1/12* (2013.01); *G01N 2030/025* (2013.01)

(56) References Cited

U.S. PATENT DOCUMENTS

| | | | |
|---|---|---|---|
| 8,100,996 | B2 | 1/2012 | Simmons et al. |
| 8,303,803 | B2 | 11/2012 | Keusenkothen et al. |
| 8,790,546 | B2 | 7/2014 | Schidt et al. |
| 9,134,663 | B2 | 9/2015 | Matsunaka et al. |
| 9,249,080 | B2 | 2/2016 | Mazanec et al. |
| 9,315,910 | B2 | 4/2016 | Eastman et al. |
| 9,368,252 | B2 | 6/2016 | Wang et al. |
| 9,777,159 | B2 | 10/2017 | Horn et al. |
| 10,479,739 | B2 | 11/2019 | Yates et al. |
| 10,486,967 | B2 | 11/2019 | Isobe et al. |
| 10,500,582 | B2 | 12/2019 | Noyes |
| 2014/0073822 | A1 | 3/2014 | Wei et al. |
| 2017/0291860 | A1* | 10/2017 | Bedard ................ C10G 50/00 |
| 2018/0142174 | A1 | 5/2018 | Grainger et al. |
| 2020/0047120 | A1 | 2/2020 | Fulde |
| 2021/0331918 | A1* | 10/2021 | Gupta ................ B01J 8/1881 |

OTHER PUBLICATIONS

Zabranska et al., "Bioconversion of carbon dioxide to methane using hydrogen and hydrogenotrophic methanogens," Elsevier, accepted Dec. 12, 2017, 15 pp.

Yates et al., "Carbon Dioxide Removal by Ionic Liquid Sorbent (CDRILS) System Development," 48th International Conference on Environmental Systems, Jul. 8-12, 2018, 15 pp.

Mitsubish Chemical, "Manufacturing Process of Carbon Black," retrieved from http://www.carbonblack.jp/en/cb/seizou.html on Mar. 22, 2021.

Isobe et al., "Carbon Dioxide Removal Technologies for U.S. Space Vehicles: Past, Present, and Future," 46th International Conference on Environmental Systems, Jul. 10-14, 2016, 10 pp.

Parkinson et al., "Hydrogen Production using Methane: Techno-Economics of Decarbonizing Fuels and Chemicals," International Journal of Hydrogen Energy, vol. 43, Issue 5, Feb. 2018, 28 pp.

U.S. Appl. No. 17/208,853, filed Mar. 22, 2021, naming inventors Michalakos et al.

* cited by examiner

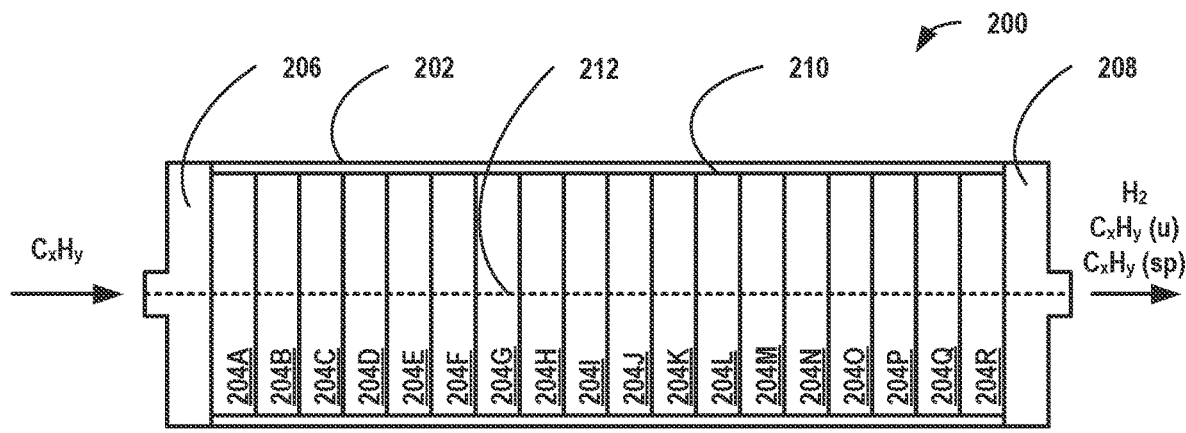
FIG. 2A
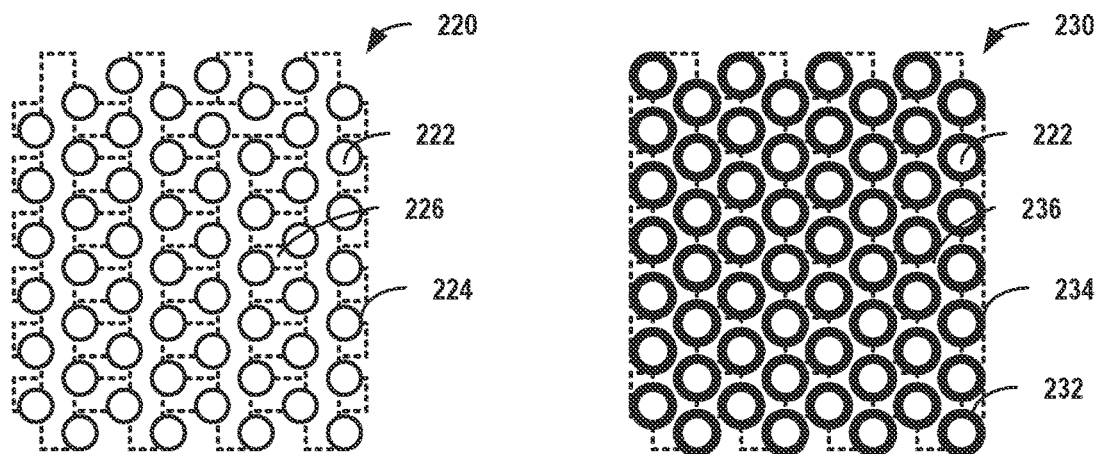
FIG. 2B
FIG. 2C

HYDROCARBON BYPRODUCT MONITORING OF FIBROUS SUBSTRATES

GOVERNMENT RIGHTS

This invention was made with Government support under Grant No. 80LARC17C0014P0000 awarded by NASA. The Government has certain rights in the invention.

TECHNICAL FIELD

The present disclosure relates to systems and techniques for collecting carbon produced during pyrolysis of hydrocarbons.

BACKGROUND

An environmental control system (ECS) of a structure, such as a building or vehicle, may remove carbon dioxide expelled by occupants of an environment, such as a room or cabin, to maintain comfort and safety. In some instances, the carbon dioxide may be absorbed from the environment by a liquid sorbent and desorbed from the liquid sorbent for discharge from the structure. However, for an atmosphere limited structure, such as a spacecraft or submarine, such discharge of carbon dioxide may waste oxygen from the carbon dioxide that may otherwise be recovered. To extract oxygen from the carbon dioxide, the ECS may react the carbon dioxide with hydrogen gas to form methane through a Sabatier reaction. The ECS may produce at least a portion of this hydrogen gas by pyrolyzing methane, which may generate solid carbon as a byproduct. Carbon generated from gas-phase reactions may form loose soot, which has a small size that may become airborne in a moving fluid or a reduced gravity environment. This soot may foul surfaces, decrease air quality, and short-circuit electrical equipment within and/or downstream of a pyrolysis reactor.

SUMMARY

In general, the disclosure describes fibrous substrates for collecting and removing carbon generated from pyrolysis of hydrocarbons. The use of such fibrous substrates may reduce soot formation, increase carbon loading capacity, and/or reduce weight. In various embodiments described herein, a pyrolysis reactor is configured to generate both hydrogen gas and solid carbon from one or more hydrocarbons, such as methane, through pyrolysis. The pyrolysis reactor may include one or more fibrous substrates that are chemically and structurally stable at high temperatures experienced during pyrolysis, such as between about 850° C. and about 1300° C.

In some examples, to encourage formation of carbon on surfaces of the fibrous substrate and reduce formation of carbon in a gas phase as soot, the fibrous substrates include a high deposition surface area for deposited carbon generated from the pyrolysis of the hydrocarbon. However, these substrates can be consumables to the chemical process, and therefore the goal is to reduce the overall weight and volume of substrates required to bring along for a given length of mission. This can be accomplished in one of two ways. First, the mass of the required number of substrates can be reduced by designing them in a way to last longer, which reduces the required amount needed. Substrate life is dictated by how long they maintain enough surface area to promote non-sooty carbon formation, and by how much loading capacity volume exists. Given a baseline fiber type, there is an inverse relationship between surface area and void fraction that must be optimized to maximize substrate life. The second way the mass of the required number of substrates can be reduced is by using lower density substrate material. Reducing substrate density can be accomplished by using less dense materials or by increasing the void fraction of the substrate. However, the void fraction must not be increased so high as to reduce the surface area of the substrate to a point that sooty carbon formation occurs, which will affect substrate life as before. Therefore, given these design requirements, independently increasing surface area without reducing void fraction, or independently reducing density without decreasing surface area would be greatly beneficial to reducing the over mass and volume of consumable substrates on a mission.

In some examples, the fibrous substrates may include fibers configured with a high ratio of surface area to volume or mass of fibrous material of the fibrous substrates, thereby increasing carbon loading and/or reducing a weight of the fibrous substrates while simultaneously maintaining high surface area and loading capacity (determined by substrate void fraction). As one example configuration, the fibers may be hollow to reduce a mass of solid substrate while maintaining a same surface area and void fraction between fibers of the fibrous substrate. As another example configuration, the fibers may have a complex cross-section, such as a multi-lobed cross-section, to increase a surface area for a particular solid fiber volume and void fraction of the fibrous substrate. As another example configuration, the fibers may have a small diameter, such as less than 10 microns, and a high packing density to increase the surface area for a particular fiber volume and void fraction of the fibrous substrate. In these various ways, the fibrous substrates described herein that include a relatively high surface area to substrate volume may reduce both an amount of soot produced during pyrolysis and an overall volume (e.g., through higher carbon loading) and/or weight (e.g., through reduced substrate mass) of the fibrous substrates consumed during a particular operation.

In some examples, the fibrous substrates may be configured to collect carbon on deposition surfaces in a manner that increases a service life of the fibrous substrates. For example, for a plug flow pyrolysis reactor in which the fibrous substrate has a flow axis between an inlet and an outlet, carbon may be generated and deposited at different rates at different axial locations in the fibrous substrates, such as due to changing surface area and substrate volume as carbon accumulates, varying concentration of hydrocarbon along the axis, varying residence time along the axis, and/or varying temperature, either radially inward toward the axis or axially along the length of the axes. This deposition of carbon may change a surface area and substrate volume of the fibrous substrate, further affecting a rate of deposition. To create a deposition profile along this flow axis that improves overall loading through the life of the fibrous substrate, the fibrous substrates may have an initial surface area or initial density that varies along the axis from the inlet to the outlet or radially outward from the axis to produce a varying rate or capacity of deposition to account for accumulation of carbon and/or varying reactor conditions as methane conversion progresses axially along the reactor. In these various ways, carbon may accumulate in the fibrous substrates in a manner that improves overall carbon loading in the fibrous substrate and extends operation of the fibrous substrates prior to soot formation.

In some examples, carbon deposition on fibrous substrates of a pyrolysis reactor may be monitored using a concentration of one or more hydrocarbon precursors to soot formation. For example, as carbon is recovered on the fibrous substrates, the fibrous substrates may become less effective as deposition media for the carbon, such as due to reduced surface area of the fibrous substrates and/or reduced void fraction of the fibrous substrates. As a result, a concentration of the hydrocarbon soot precursors, such as acetylene or benzene, may change (e.g., increase and/or decrease). A control system of the pyrolysis reactor may measure the concentration of one or more hydrocarbon soot precursors for use as an indication as to a rate or extent of carbon deposition of the fibrous substrates in the pyrolysis reactor. As one example, the concentration of one or more hydrocarbon soot precursors may indicate that the fibrous substrates must be replaced, and may be used to initiate bringing the pyrolysis reactor offline for maintenance. As a result, the fibrous substrates may be operated with a smaller margin of error for service life and/or may be operated with less soot production. As another example, the concentration of one or more hydrocarbon precursors may indicate a rate of carbon deposition in the pyrolysis reactor, and may be used to actively control one or more operating conditions of the pyrolysis reactor, such as an axial temperature profile of the pyrolysis reactor or a flow rate to the pyrolysis reactor. As a result, the fibrous substrate may be more fully loaded prior to be replaced.

In some examples, the disclosure describes a system for generating hydrogen gas from pyrolysis of a hydrocarbon with reduced soot formation and increased carbon loading. The system includes a pyrolysis reactor configured to generate the hydrogen gas from the hydrocarbon through pyrolysis. The pyrolysis reactor includes one or more fibrous substrates defining a deposition surface for carbon generated from the pyrolysis of the hydrocarbon. Each fibrous substrate of the one or more fibrous substrates has an effective void fraction between 40% and 95% and includes a plurality of fibers configured to maintain chemical and structural stability between 850° C. and 1300° C. The one or more fibrous substrates may have a relatively high surface area to substrate and/or reactor volume.

In some examples, the disclosure describes a method for generating hydrogen gas from pyrolysis of a hydrocarbon with reduced soot formation and increased carbon loading. The method includes receiving, by a pyrolysis reactor, the hydrocarbon and pyrolyzing, by the pyrolysis reactor, the hydrocarbon to generate the hydrogen gas and carbon. The pyrolysis reactor includes one or more fibrous substrates defining a deposition surface for carbon generated from the pyrolysis of the hydrocarbon. Each fibrous substrate of the one or more fibrous substrates has an effective void fraction between 40% and 95% and includes a plurality of fibers configured to maintain chemical and structural stability between 850° C. and 1300° C.

In some examples, the disclosure describes a system for generating hydrogen gas that includes one or more pyrolysis reactors configured to generate the hydrogen gas from a hydrocarbon through pyrolysis. Each pyrolysis reactor of the one or more pyrolysis reactors includes one or more fibrous substrates and a concentration sensor downstream of at least one fibrous substrate of the one or more fibrous substrates. Each fibrous substrate of the one or more fibrous substrates defines a deposition surface for carbon generated from the pyrolysis of the hydrocarbon and includes a plurality of fibers configured to maintain chemical and structural stability between 850° C. and 1300° C. The concentration sensor is configured to measure a concentration of one or more hydrocarbon byproducts or soot precursors, such as acetylene.

In some examples, the disclosure describes a method for generating hydrogen gas that includes pyrolyzing, by one or more pyrolysis reactors, a hydrocarbon to generate the hydrogen gas and carbon. Each pyrolysis reactor of the one or more pyrolysis reactors includes one or more fibrous substrates and a concentration sensor downstream of at least one fibrous substrate of the one or more fibrous substrates. Each fibrous substrate of the one or more fibrous substrates defines a deposition surface for carbon generated from the pyrolysis of the hydrocarbon and includes a plurality of fibers configured to maintain chemical and structural stability between 850° C. and 1300° C. The concentration sensor is configured to measure a concentration of one or more hydrocarbon byproducts or soot precursors.

The details of one or more examples are set forth in the accompanying drawings and the description below. Other features, objects, and advantages will be apparent from the description and drawings, and from the claims.

BRIEF DESCRIPTION OF THE FIGURES

The details of one or more examples are set forth in the accompanying drawings and the description below. Other features, objects, and advantages will be apparent from the description and drawings, and from the claims.

FIG. 2A is a schematic block diagram illustrating an example pyrolysis reactor for generating hydrogen gas from hydrocarbons.

FIG. 2B is a cross-sectional front view diagram illustrating an example simplified, unloaded fibrous substrate for collecting carbon generated during pyrolysis.

FIG. 2C is a cross-sectional front view diagram illustrating an example simplified, partially loaded fibrous substrate for collecting carbon generated during pyrolysis.

DETAILED DESCRIPTION

In general, this disclosure describes fibrous substrates for collecting carbon produced during pyrolysis, and systems and techniques that employ the same. Pyrolysis of hydrocarbons, such as methane and ethane, produces hydrogen gas and carbon. Carbon that is produced in a gas phase may form as suspended soot, which may foul surfaces or passages downstream of the fibrous substrates. To reduce an amount of carbon formed as soot, fibrous substrates described herein may include a surface with high surface area on which the carbon may form through heterogeneous nucleation processes, such as chemical vapor deposition. However, as carbon collects on the fibrous substrates and the solid volume of the fibrous substrates increase, the void fraction of the fibrous substrates may be reduced. For example, while initially deposition of carbon on fibers of the fibrous substrate may increase a surface area on which the carbon may collect (e.g., by increasing a diameter of the fibers), eventually the collected carbon may reduce a porosity of the fibrous substrates and/or increase a closed porosity of the fibrous substrates (e.g., by blocking voids and creating pockets of inaccessible surface area). Without adequate surface area available for the carbon to deposit, soot may begin to form and the fibrous substrate may be swapped out with an unloaded fibrous substrate. Throughout a particular operation, the accumulation of these loaded fibrous substrates may represent a significant volume and mass, and clean-up of soot may represent a significant maintenance and operational cost.

According to some examples of the disclosure, fibrous substrates described herein may provide both a relatively high surface area for encouraging carbon deposition and a high void fraction for allowing carbon accumulation, such that the fibrous substrate may have relatively low soot formation, long operational life, and/or reduced weight. The fibrous substrates may include various fiber properties, such as diameter or shape, that provide a high surface area for carbon deposition for a particular substrate volume. The fibrous substrates may include various fiber properties that vary according to anticipated local and dynamic conditions that affect a rate of carbon deposition, such as a temperature gradient across or along a bundle of fibers, a concentration reduction as the reactant gas passes through the pyrolysis reactor, or a surface area or void fraction change as carbon accumulates in particular portions of the fibrous substrates. As will be described further below, such fibrous substrates may enable a pyrolysis reactor to produce hydrogen gas without downstream filtration and may have a longer surface life compared to denser or lower surface area substrates.

Figure 1A:
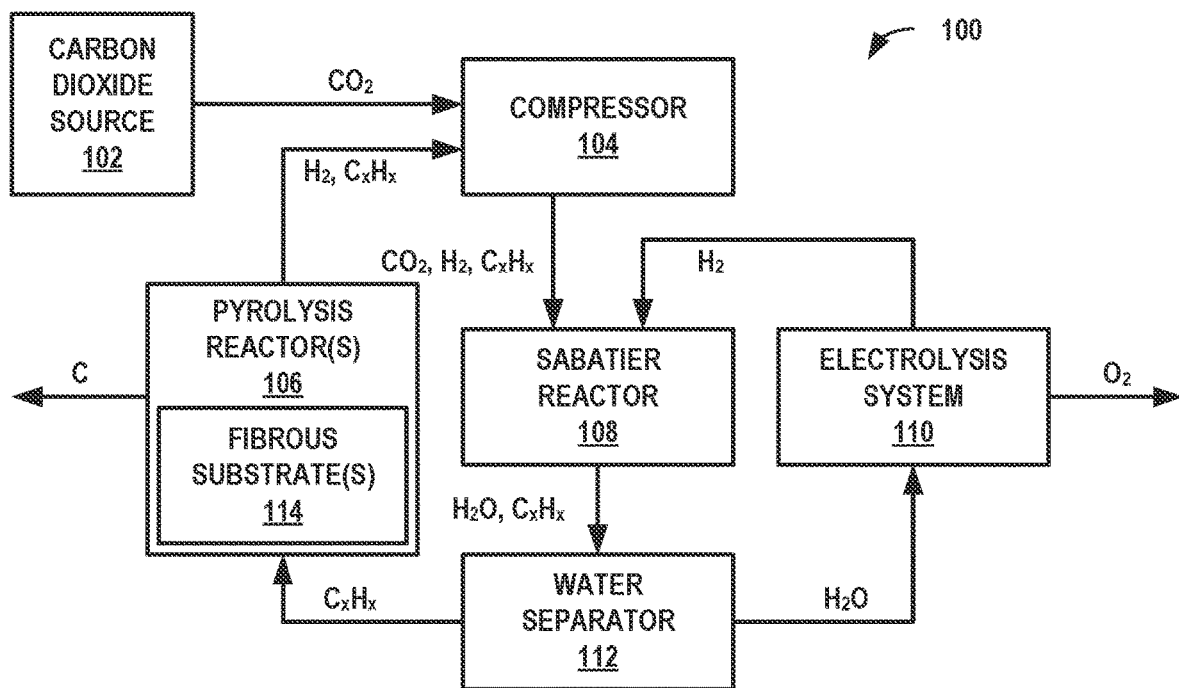
FIG. 1A is a schematic block diagram illustrating an example for generating oxygen from carbon dioxide.

In some instances, fibrous substrates described herein may be utilized in aerospace applications, such as spacecraft. For example, a spacecraft may include a resource-limited and weight- and volume-sensitive environment for which resources like oxygen and water may be preserved in closed loop processes. FIG. 1 is a schematic block diagram illustrating an example system 100 for generating oxygen from carbon dioxide produced in a spacecraft. While fibrous substrates will be described with respect to one or more processes of system 100, the fibrous substrates described herein may be used with a variety of processes in which carbon may be effectively captured from pyrolysis of hydrocarbons. For example, hydrocarbons discharged as waste during various industrial processes may be pyrolyzed to produce hydrogen gas and low soot carbon feedstocks.

System 100 may include a carbon dioxide source 102. Carbon dioxide source 102 may be configured to receive carbon dioxide from an environment, such as a spacecraft cabin, concentrate the carbon dioxide for use as a recoverable oxygen source, and discharge purified air back to the spacecraft cabin. For example, carbon dioxide source 102 may include a carbon dioxide removal assembly (CDRA) or other carbon dioxide separation system.

System 100 may include a compressor 104. Compressor 104 may be configured to receive gases from various sources, such as carbon dioxide source 102 and one or more pyrolysis reactors 106, and compress the gases to an operating pressure of a Sabatier reactor 108. For example, Sabatier reactor 108 may operate at relatively higher pressures than carbon dioxide source 102 or pyrolysis reactors 106. In some examples, compressor 104 may be configured to create and maintain a vacuum in pyrolysis reactors 106.

System 100 may include Sabatier reactor 108. Sabatier reactor 108 may be configured to receive hydrogen gas, carbon dioxide, and optionally other hydrocarbon gasses, and generate water and hydrocarbons, such as methane and ethane. For example, Sabatier reactor 108 may be configured to receive hydrogen gas from pyrolysis reactors 106 and an electrolysis system 110, and carbon dioxide from carbon dioxide source 102, as well as other hydrocarbon gases, such as unreacted saturated hydrocarbons or byproduct unsaturated hydrocarbons from pyrolysis reactors 106. Sabatier reactor 108 may be configured to operate at a relatively moderate temperature and pressure, such as about 400° C. and about 100 kPa, and may include a catalyst or other rate-enhancing material or structure. Sabatier reactor 108 may be configured to operate according to the following exothermic reaction:

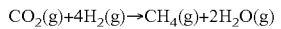

$$CO_2(g) + 4H_2(g) \rightarrow CH_4(g) + 2H_2O(g)$$

System 100 may include a water separator 112 downstream of Sabatier reactor 108. Water separator 112 may be configured to receive water and hydrocarbons, such as methane and ethane, from Sabatier reactor 108 and separate the water from the hydrocarbons. Water separator 112 may be configured to discharge at least a portion of the water to electrolysis system 110 and at least a portion of the hydrocarbons to pyrolysis reactors 106. In some instances, a water discharged to pyrolysis reactors 106 may be substantially low (e.g., less than 1 vol. %). A variety of water separators may be used including, but not limited to, condensers, centrifugal separators, membranes (e.g., zeolite membranes), and the like.

As one hydrogen source for Sabatier reactor 108, system 100 may include an oxygen generation assembly, such as electrolysis system 110. Electrolysis system 110 may be configured to receive water from various sources, such as Sabatier reactor 108 or a potable water source and generate oxygen gas and hydrogen gas from the water. Electrolysis system 110 may be configured to discharge the hydrogen gas back to Sabatier reactor 108 and discharge oxygen gas to a storage or pressurization system for use in one or more environments. Electrolysis system 110 may be configured to operate according to the following reaction:

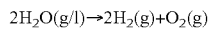

As described above, water separator 112 may be configured to discharge hydrocarbons generated from Sabatier reactor 108 to one or more pyrolysis reactors 106. In other oxygen generation systems that generate oxygen from carbon dioxide, carbon and hydrogen may be expended by discharging any hydrocarbons generated in a Sabatier reactor overboard. As a result of discharging hydrogen, an amount of hydrogen gas available to react in the Sabatier reactor may be reduced, thereby limiting recovery of oxygen. In contrast, system 100 may be configured to preserve at least a portion of the hydrogen present in hydrocarbons from Sabatier reactor 108 by sending the hydrocarbons through one or more pyrolysis reactors 106 to produce hydrogen gas.

Pyrolysis reactor(s) 106 may each be configured to generate hydrogen gas from hydrocarbons through pyrolysis. In the example of FIG. 1, pyrolysis reactors 106 may be configured to generate hydrogen gas and carbon from methane, such as according to the following endothermic reaction:

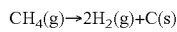

Each pyrolysis reactor 106 includes one or more fibrous substrates 114. Each fibrous substrate 114 may be configured to provide a deposition surface for carbon generated from the pyrolysis of the hydrocarbons. In some examples, fibrous substrates 114 may be configured to be removable from pyrolysis reactors 106 once loaded and replaced with a new fibrous substrate 114. As will be explained further below, fibrous substrates 114 may be configured with a relatively high surface area to substrate volume and/or substrate mass, such that fibrous substrates 114 may reduce soot formation.

Pyrolysis reactors 106 may be configured to continuously remove carbon produced during pyrolysis using fibrous substrates 114. For example, while pyrolysis reactors 106 are illustrated as a single pyrolysis reactor, pyrolysis reactors 106 may include two or more pyrolysis reactors, such that one or more pyrolysis reactors 106 may be taken offline to replace fibrous substrates 106 while the other pyrolysis reactors 106 may continue to operate.

Figure 1B:
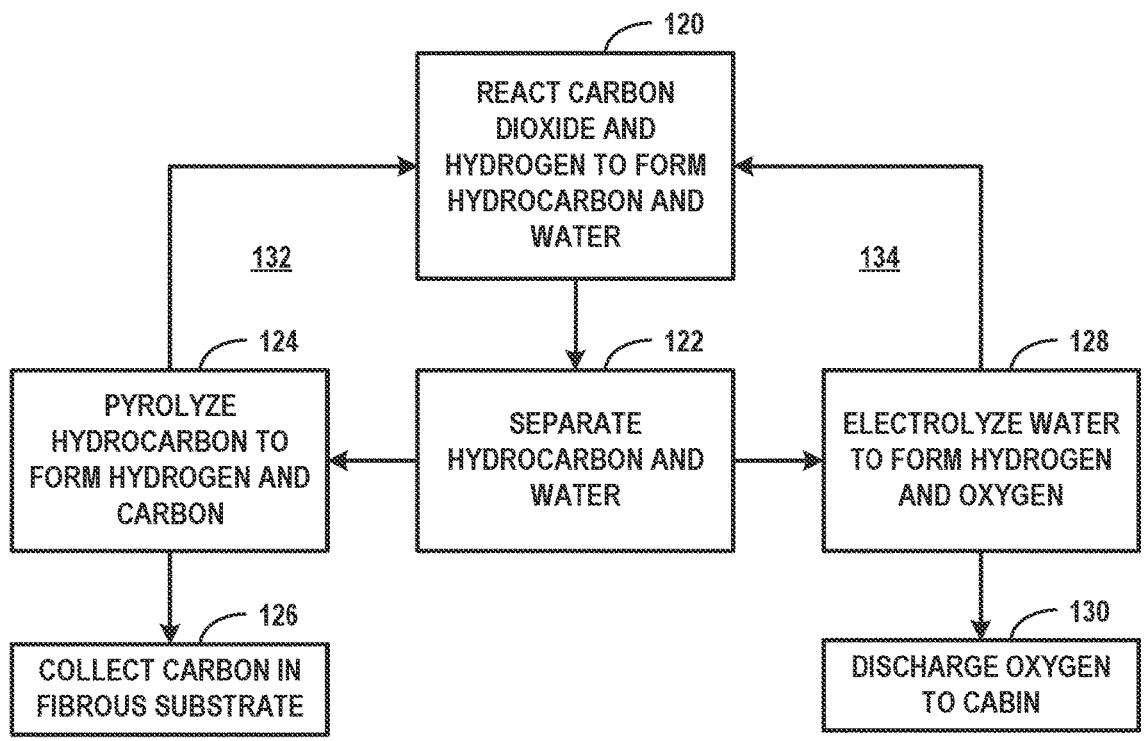
FIG. 1B is a flowchart of an example technique for generating oxygen from carbon dioxide.

FIG. 1B is a flowchart of an example technique for generating oxygen from carbon dioxide. The example technique of FIG. 1B will be described with reference to system 100 of FIG. 1A; however, the example technique of FIG. 1B may be performed by other systems. The technique of FIG. 1B includes a carbon recovery cycle 132 and an oxygen recovery cycle 134. While carbon recovery cycle 132 and oxygen recovery cycle 134 will be referred to as separate cycles based on discharged products, it will be understood that hydrogen may be recovered in both cycles 132 and 134, and that recovery of hydrogen in both cycles may enable more complete recovery of oxygen and/or carbon in cycles 134 and 132, respectively.

In both carbon recovery cycle 132 and oxygen recovery cycle 134, Sabatier reactor 108 may react carbon dioxide and hydrogen to form one or more hydrocarbons and water (120). For example, Sabatier reactor 108 may receive carbon dioxide from carbon dioxide source 102 and hydrogen gas and, optionally, hydrocarbons from pyrolysis reactors 106 via compressor 104. Sabatier reactor 108 may react the carbon dioxide and hydrogen gas under operating conditions, such as about 400° C. and about 100 kPa. Sabatier reactor 108 may discharge water and hydrocarbons, such as methane and ethane, to water separator 112. In some examples, the hydrocarbons discharged to water separator 112 includes greater than 90 vol. % methane.

Water separator 112 may separate hydrocarbons and water (122). For example, water separator 112 may receive hydrocarbons and water from Sabatier reactor 108 and use one or more phase change, filtration, or other separation processes to separate hydrocarbons and water. Water separator 112 may discharge at least a portion of the hydrocarbons to pyrolysis reactors 106 and at least a portion of the water to electrolysis system 112. In some examples, the stream discharged to pyrolysis reactors 106 includes less than 1 vol. % water.

In oxygen recovery cycle 134, electrolysis system 128 may electrolyze water to hydrogen and oxygen (128). For example, electrolysis system 128 may receive water from Sabatier reactor 108 via water separator 112, and optionally other water sources such as dehumidification systems. Electrolysis system 128 may discharge hydrogen gas back to Sabatier reactor 108 to further react with carbon dioxide (120). In some examples, the hydrogen gas generated from electrolysis system 128 may account for about half (e.g., between about 40% and about 60%) of the hydrogen gas reacted in Sabatier reactor 108. Electrolysis system 128 may discharge oxygen to a cabin (130) or storage system to complete recovery of the oxygen received as carbon dioxide.

In carbon recovery cycle 132, pyrolysis reactors 106 may pyrolyze hydrocarbons to form hydrogen and carbon (124). For example, pyrolysis reactors 106 may receive hydrocarbons from Sabatier reactor 108 via water separator 112 and pyrolyze the hydrocarbons under pyrolysis operating conditions, such as a temperature between about 850° C. and about 1300° C., and preferably between about 1050° C. and about 1200° C., and a pressure between about 1 kPa and about 65 kPa, and preferably between about 7 kPa and about 30 kPa, to form hydrogen gas and carbon. Pyrolysis reactors 106 may discharge hydrogen gas, and optionally unreacted or partially reacted hydrocarbons, to Sabatier reactor 108 to further react with carbon dioxide (120). Pyrolysis reactors 106 may capture the carbon in fibrous substrates 106 (126), which may be removed from pyrolysis reactors 106 at an end of an operating life (e.g., initiation of soot formation, as will be explained further below), replaced, and stored.

As will be described herein, pyrolysis reactors 106 that use fibrous substrates 114 may be configured to reduce an amount of soot generated during pyrolysis and operate for a relatively long life. FIG. 2A is a schematic block diagram illustrating an example pyrolysis reactor 200 for generating hydrogen gas from hydrocarbons, such as may be used for pyrolysis reactors 106 of FIG. 1.

Pyrolysis reactor 200 includes a pyrolysis chamber 202, an inlet 206 at a first end for receiving gases into pyrolysis chamber 202, and an outlet 208 at a second end for discharging gases from pyrolysis chamber 202. Inlet 206 and outlet 208 may define an axis 214 of pyrolysis reactor 200. In the example of FIG. 2A, pyrolysis reactor 200 may be configured for general plug flow along axis 212, such that hydrocarbon gases may be continuously received and hydrogen gases continuously discharged from pyrolysis reactor 200; however, in other examples, pyrolysis reactor 200 may include a mixed design, such as mixed flow within a reactor volume for a particular residence time. Pyrolysis chamber 202 may be sized to have a particular residence time for a particular flow rate of gases and particular void fraction or pressure drop of fibrous substrates.

Pyrolysis chamber 202 may be configured to house one or more fibrous substrates 204A, 204B, 204C, 204D, 204E, 204F, 204G, 204H, 204I, 204H, 204K, 204L, 204M, 204N, 204O, 204P, 204Q, 204R (individually "fibrous substrate 204" and collectively "fibrous substrates 204"). While pyrolysis chamber 202 is illustrated as including fibrous substrates 204 having a stacked arrangement in series and a puck shape, fibrous substrates 204 may include any arrangement, including elongated shape or parallel arrangement. An interior volume of pyrolysis chamber 202 may be accessible such that fibrous substrates 204 may be removed and replaced as needed. In operation, gas may flow from a first end at inlet 206 into pyrolysis chamber 202, through one or more fibrous substrates 204 along flow axis 214, and from pyrolysis chamber 202 to outlet 208 at a second end. In some examples, pyrolysis chamber 202 may include one or more bypass channels around fibrous substrates 204, such as to control a flow rate of gas through pyrolysis chamber 202.

In some examples, pyrolysis reactor 200 may include one or more structures 212 between and/or around substrates 204. Structures 210 may be configured to position fibrous substrates 204 and/or provide support to fibrous substrates 204. For example, while not shown in FIG. 2A, structures 210 may be configured to position fibrous substrates 204 within pyrolysis chamber 202, such as in a hexagonal or other configuration that may permit access to fibrous substrates 204 for removal. In some examples, pyrolysis reactor 200 may include one or more heat sources configured to heat a volume of pyrolysis chamber 202.

Each fibrous substrate 204 includes a plurality of fibers. FIG. 2B is a cross-sectional front view diagram illustrating an example portion 220 of fibrous substrate 204 for collecting carbon generated during pyrolysis. Portion 220 includes a plurality of fibers 222. While FIG. 2B illustrates fibers 222 as evenly spaced and aligned along and perpendicularly across axis 212 for simplicity of explanation, in other examples, fibers 222 may be present in other configurations, including woven, non-woven, tangled, meshed, and the like.

Fibers 222 may be configured to operate under operating conditions for pyrolysis of hydrocarbons. In some examples, fibers 222 may have a relatively high melting or thermal degradation temperature, so as to maintain structural stability throughout the entire range of possible pyrolysis temperatures. In some examples, fibers 222 may have a relatively low material density to reduce a weight of fibrous substrates 204. A variety of materials may be used for fibers 222 including, but not limited to, carbon, zirconium dioxide (zirconia), silicon dioxide (silica), and the like.

In some examples, fibers 222 may form a fibrous substrate 204 that is self-supporting. For example, any support or other surface withing pyrolysis chamber 202 may accumulate carbon. By including fibers that form a self-supporting substrate, fibrous substrate 204 may reduce a surface area within pyrolysis chamber 202 that is not removable from pyrolysis chamber 202 or simplify cleaning or other maintenance between loading fibrous substrates 204. In some examples, fibers 222 may include carbon fibers that form a self-supporting fibrous substrate 204. For example, a fully carbon loaded fibrous substrate 204 may include relatively pure, soot-free carbon that includes both the carbon fibers of fibrous substrate 204 and carbon deposited on the carbon fibers from pyrolysis.

The plurality of fibers 222 may be configured and arranged to remove carbon with reduced soot formation. Without being limited to any particular theory, during pyrolysis at high temperatures, hydrocarbons such as methane may lose hydrogen to form various two-carbon intermediates, such as acetylene ($C_2H_2$). Acetylene may react with a deposition surface 224 of fibers 222 to form deposited carbon and/or react in a gas phase to form various derivatives, such as benzene or larger unsaturated hydrocarbons, eventually forming soot. The rates of both the surface reaction of acetylene and the gas phase reaction may be proportional to a concentration of acetylene in the gas phase (and similarly for the various derivatives of acetylene); however, the surface reaction may be further proportional to an available surface area to which the acetylene may diffuse and deposit. To increase deposition of carbon and reduce formation of soot, fibrous substrates 204 may be configured to provide a sufficiently high surface area for a particular volume of gas, such that intermediates of pyrolyzed hydrocarbons favor surface reactions on fibers 222 of fibrous substrates 204.

Each fiber 222 includes deposition surface 224 for carbon generated from the pyrolysis of hydrocarbons in pyrolysis reactor 200 to deposit. The cumulative deposition surfaces 224 of the plurality of fibers 222 that are accessible to hydrocarbons may provide a surface area of fibrous substrate 204. As will be described further below, this surface area may be increased to enhance deposition of carbon on deposition surfaces 224 of the plurality of fibers 222 during pyrolysis.

Portion 220 may include an open volume 226 between the plurality of fibers 222. The cumulative open volume 226 between the plurality of fibers 222 may provide a void fraction of fibrous substrate 204 (or, conversely, a solid volume of fiber of fibrous substrate 204). The surface area of fibrous substrate 204 may be relatively high for a particular volume of hydrocarbon gas being reacted, thus favoring heterogeneous nucleation of carbon of fibers 222. A fibrous substrate 204 having a low density (and correspondingly, high open volume 226) may generate soot, as fibrous substrate 204 may not have sufficient available surface area for the carbon generated from hydrocarbons in open volume 226 to deposit. To increase a relative surface area to open volume 226, fibers 222 in fibrous substrate 204 may be present in a sufficiently high density to produce a relatively high surface area for a particular volume of substrate 204. In some examples, the plurality of fibers 222 may have an effective void fraction between 40% and 95%.

During deposition of carbon from pyrolysis, a surface area and void fraction (or correspondingly, solid volume) of fibrous substrates 204 may change. FIG. 2C is a cross-sectional front view diagram illustrating an example fibrous substrate for collecting carbon generated during pyrolysis. While the example of FIG. 2B illustrates portion 220 of fibrous substrate 204 prior to pyrolysis, the example of FIG. 2C illustrates an equivalent portion 230 of fibrous substrate 204 during pyrolysis after partial loading.

As pyrolysis proceeds, a layer of deposited carbon 232 forms on fibers 222. Deposited carbon 232 may have a surface 234 upon which more carbon may deposit. As deposited carbon 232 forms on fibers 222, a surface area of surface 234 may initially increase. However, eventually a surface area of surface 234 may begin to decrease, such as by producing closed pores within porous substrate 204 or joining or merging to adjacent fibers 222. Eventually, the deposition surface of the plurality of fibers 222 may not provide sufficient surface area for carbon to deposit for the amount of hydrocarbon being reacted, and soot may begin to form, indicating replacement of fibrous substrate 204 is required.

As explained above, to improve carbon loading while reducing soot formation, fibrous substrates 204 may be configured with a high ratio of surface area of fibers 222 to volume of fibrous substrates 204 and/or a high ratio of surface area of fibers 222 to mass of fibrous substrates 204. FIGS. 3A-3D illustrate various properties of fibers 222 that may increase a relative surface area to volume or mass of fibers of the fibrous substrate.

Figure 3A:
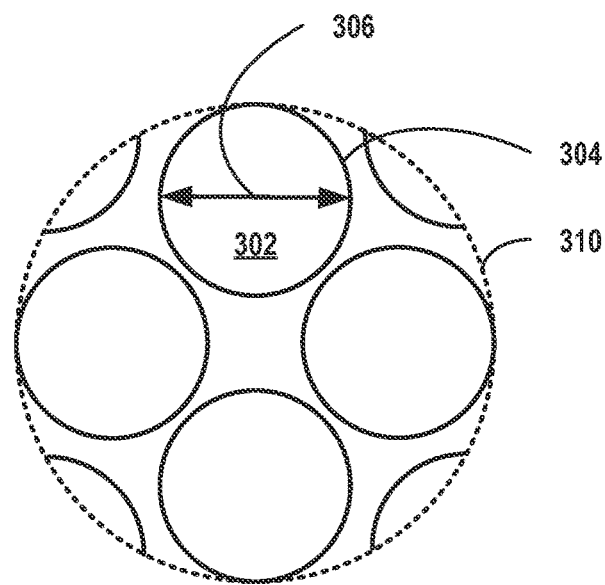
FIG. 3A is a diagram illustrating an example hollow fiber for a fibrous substrate for a pyrolysis reactor.

In some examples, fibrous substrates may include a large number of reduced diameter fibers. FIG. 3A is a diagram illustrating an example reduced diameter fiber for a fibrous substrate for a pyrolysis reactor. Each fiber 302 has a surface area 304 (represented by a perimeter in the cross-section of FIG. 3A) and a diameter 306. For illustration purposes, FIG. 3A includes a comparative fiber 310 having a relatively large diameter, such as 2.5 times diameter 306 of fiber 302. Fibers 302 in a cross-sectional area corresponding to fiber 310 may be packed together and may occupy a similar fiber volume as fiber 310, and thereby similar density as fiber 310, while maintaining a larger surface area 304 (illustrated as a perimeter). In some examples, the plurality of fibers has an average fiber diameter that is less than about 10 microns, such as less than 5 microns.

Figure 3B:
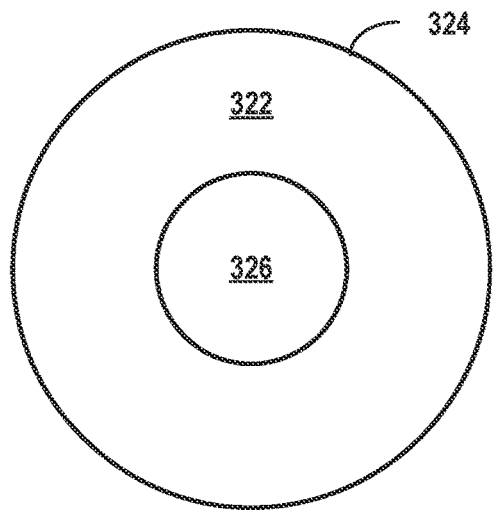
FIG. 3B is a diagram illustrating an example reduced diameter fiber for a fibrous substrate for a pyrolysis reactor.

In some examples, fibrous substrates may include a high surface area for a particular mass of fibers 222 by reducing an overall mass density of fibers 222. FIG. 3B is a diagram illustrating an example hollow fiber for a fibrous substrate for a pyrolysis reactor. Fiber 320 include a lumen 326 in a center of fiber 320 and a surface area 324 (illustrated as a perimeter). Fiber 320 may have a same outer surface area 324 as an equivalent solid fiber, but may have a reduced solid fiber volume, and thereby weight, due to the presence of lumen 326. For example, lumen 326 may not be accessible to hydrocarbon gases to react, or may be accessible early in pyrolysis and may become blocked as carbon accumulates, thereby providing additional surface area early in pyrolysis and reducing void fraction later in pyrolysis. As such, lumen 326 may not contribute to an open volume or surface area of a corresponding fibrous substrate, such that the fibrous substrate may still maintain a relatively high surface area to substrate volume.

Figure 3C:
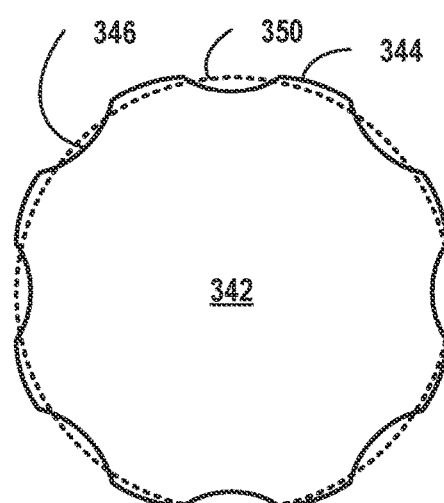
FIG. 3C is a diagram illustrating an example serrated surface fiber for a fibrous substrate for a pyrolysis reactor.
Figure 3D:
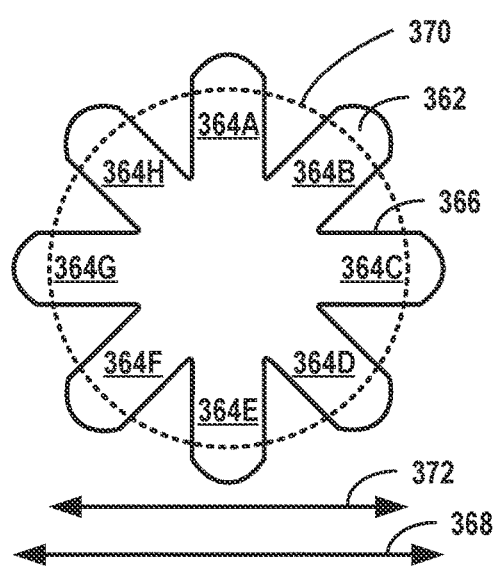
FIG. 3D is a diagram illustrating an example multi-lobal fiber for a fibrous substrate for a pyrolysis reactor.

In some examples, such as will be illustrated in FIGS. 3C and 3D, fibrous substrates may include a high surface area for a particular volume of fibers by using fibers having a complex shape with a high surface area. For example, a ratio of surface area to volume of individual fibers may be increased by incorporating fibers having a non-circular cross-section that increases a ratio of surface area to diameter. Dimensional complexity of the fibers may be represented by a variety of measures of geometric complexity including, but not limited to, a ratio of a surface area of a fiber to a volume of solid material of the fiber, a ratio of surface area of the fiber to an average diameter of the fiber, a ratio of a maximum diameter of the fiber to an average diameter of the fiber, a length of a perimeter (or circumference) of the fiber to an average diameter of the fiber, an algebraic complexity (e.g., a measure of a degree of polynomials for representing the surface of the fiber), a morphological complexity (e.g., a measure of local surface variation of the fiber), a combinatorial complexity (e.g., a measure of vertexes in polygonal meshes representing the surface of the fiber), and the like.

In some examples, the fibers may include surface variations that increase irregularities, and therefore surface area, of the fibers. FIG. 3C is a diagram illustrating an example serrated surface fiber for a fibrous substrate for a pyrolysis reactor. Fiber 342 may include a surface area 346 (illustrated as a perimeter) and one or more raised (or alternatively, lowered) portions 344 that deviate from an even radius (i.e. circle) from a center of fiber 342. For example, fiber 342 may be formed as a round fiber and surface treated to form portions 344. For illustration purposes, FIG. 3C includes a comparative fiber 350 having a consistent radius and an equivalent volume. For the same volume, fiber 342 includes a higher surface area, and may accumulate carbon in a manner that preserves some contour of the raised or lowered portions 344.

In some examples, the fibers may include a complex shape. A complex shape may include a shape that has a high surface area (3-dimensional) or perimeter (2-dimensional) relative to a volume (3-dimensional) or diameter (2-dimensional). FIG. 3D is a diagram illustrating an example multi-lobal fiber for a fibrous substrate for a pyrolysis reactor. Fiber 362 may include a surface area 366 (illustrated as a perimeter) and one or more lobes 364A, 364B, 364C, 364D, 364E, 364F, 364G, 364H (individually "lobe 364" and collectively "lobes 364") that deviate from a radius (i.e. circle) from a center of fiber 342. Lobe 364 may include any projection or other feature in which a radius of lobe 364 (or diameter of two opposite lobes 364) is greater than an average radius (or diameter) of fiber 362. For example, fiber 362 may have a maximum diameter 368 across two lobes 364 and an average diameter 372. For illustration purposes, FIG. 3D includes a comparative fiber 370 having a diameter of average diameter 372 and an equivalent volume as fiber 362. For the same volume, fiber 362 includes a higher surface area. While illustrated as a multi-lobed design, fiber 362 may have a variety of shapes. In some examples, maximum diameter 368 of fiber 362 is at least 25% greater than average diameter 372 of fiber 362. In some examples, a perimeter (corresponding to a surface area) of a cross-section of fiber 362 is at least four times as great as average diameter 372 of fiber 362.

Figure 4A:
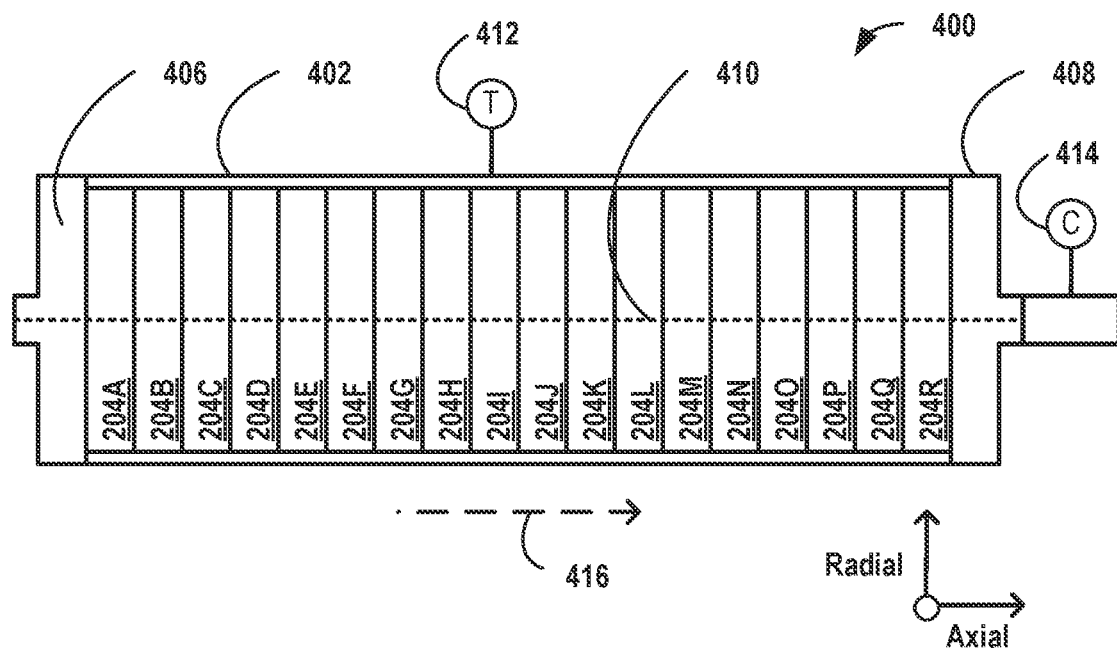
FIG. 4A is a cross-sectional side view diagram illustrating an example pyrolysis reactor having one or more axial gradients.

Pyrolysis reactors described herein may carbon deposition rates that vary spatially within fibrous substrates and temporally as fibrous substrates accumulate carbon. FIG. 4A is a cross-sectional side view diagram illustrating an example pyrolysis reactor 400. Pyrolysis reactor 400 may include a pyrolysis chamber 402, fibrous substrates 404, an inlet 406, an outlet 408, and a flow axis 410 that may be operationally and structurally similar to pyrolysis chamber 202, fibrous substrates 204, inlet 206, outlet 208, and flow axis 210 of FIG. 2A.

Pyrolysis reactor 400 may include process measurement instrumentation, such as one or more concentration sensors 414, temperature sensors 410, and the like. Concentration sensors 414 may be configured to measure a concentration of one or more gases within or exiting pyrolysis reactor 400. For example, concentration sensors 414 may be configured to measure a concentration of unreacted hydrocarbons, such as methane; product gases, such as hydrogen gas; and/or hydrocarbon byproducts or soot precursors, such as acetylene or benzene. While illustrated as being downstream of pyrolysis reactor 400, in some instances, concentration sensors 414 may be configured to measure a concentration of gases within pyrolysis reactor 400, such as along axis 410, such that concentration sensor 414 may provide an indication of carbon accumulation and/or rate of carbon deposition at different axial locations along axis 410 or in different fibrous substrates 404 along axis 410. Temperature sensors may be configured to measure a temperature of one or more gases or fibrous substrates 404 within pyrolysis reactor 400. While illustrated as being on a surface of pyrolysis reactor 400, in some instances, temperature sensors 412 may be configured to measure a temperature of gases within pyrolysis reactor 400, such as along axis 410, such that temperature sensors 412 may provide an indication of temperature along axis 410 or in different fibrous substrates 404 along axis 410.

In some examples, pyrolysis reactor 400 may operate at one or more axial gradients 416 along flow axis 410. Axial gradients 416 may be inherent in a plug flow design of pyrolysis reactor 400 and/or a chemistry of the pyrolysis reaction within pyrolysis reactor 400. The various axial gradients 416 may cumulatively influence the rate of carbon deposition along axis 410. In some examples, axial gradient 416 may include any operating condition of pyrolysis reactor 400 that varies by greater than about 10% during operation of pyrolysis reactor 400, such as a temperature within pyrolysis chamber 402 or a concentration of reactants (e.g., hydrocarbon) or products (e.g., hydrogen gas or hydrocarbon) in pyrolysis chamber 402.

In some instances, axial gradient 416 may include a temperature gradient or curve along axis 410. For example, a temperature within pyrolysis reactor 400 may increase from inlet 406 to near a middle of pyrolysis chamber 402 and decrease from the middle of pyrolysis chamber 402 to outlet 408. As temperature increases, a rate of the endothermic pyrolysis reaction increases, thereby increasing a rate of carbon deposition on fibrous substrates 404. In some instances, axial gradient 416 may include a concentration gradient or curve along axis 410. For example, a concentration of methane may decrease and a concentration of hydrogen gas may increase as more methane is converted to hydrogen gas. As a concentration of reactants (methane) decreases and a concentration of products (hydrogen gas) increases, a rate of carbon deposition may decrease. In some instances, axial gradient 416 may include a flow rate gradient or curve along axis 410. For example, a flow rate of the gas in pyrolysis reactor 200 may increase with increasing methane conversion, as 1 mole of methane generates two moles of hydrogen. As a flow rate increases and residence time decreases, a rate of carbon deposition may decrease.

As a result of the various axial gradients 416 on the rate of carbon deposition, fibrous substrates 404 may accumulate carbon unevenly along axis 410. A surface area of fibrous substrates 404 and/or a residence time of hydrocarbons within fibrous substrates 404 may change as carbon accumulates on fibrous substrates 404. For fibrous substrates 404 having a uniform density, this uneven accumulation may cause a substantial reduction in surface area or residence time at fibrous substrates 404 at particular axial positions along axis 410, leading to replacement of fibrous substrate 404 prior to full or substantially full loading of substrate 404.

In some examples, pyrolysis reactor 400 may be configured to actively control a rate of carbon deposition along axis 410 by controlling an axial temperature profile. Pyrolysis reactor 400 may include one or more heaters configured to produce varying amounts of heat along axes 404 to heat fibrous substrates 404 according to an axial temperature profile. This axial temperature profile may control a rate of carbon deposition at various portions of fibrous substrate 404 along axes 414, such that fibrous substrate 404 may accumulate a greater amount of carbon prior to being replaced compared to a fibrous substrate that does not include a controlled axial temperature profile.

In some examples, fibrous substrates 404 may be configured with an initial surface area or density that varies along the respective axes 414, such that fibrous substrates 404 may be configured to passively control a rate of carbon deposition along axes 414. In some instances, an initial surface area or density of fibrous substrates 404 may be increased (or corresponding initial void fraction of fibrous substrates 404 decreased) in particular axial portions of fibrous substrates 404 that may receive a higher rate of carbon deposition than other portions, such as portion of fibrous substrates 404 at a higher temperature or near outlet 408. For example, fibrous substrates 404 (or portions of fibrous substrates 404 for parallel fibrous substrates 404) may have a higher void fraction near inlet 406 of pyrolysis reactor 400 and a lower void fraction near outlet 408 of pyrolysis reactor 400. As a result, fibrous substrates 404 may accumulate a greater amount of carbon prior to being replaced compared to a fibrous substrate that does not include an axially varying initial surface area or density. Fibrous substrates 404 may vary an initial surface area or density using any of the principles described in FIGS. 3A-3D, such as by incorporating lower diameter fibers or complex surface area fibers at an equivalent fiber volume to increase surface area.

Figure 4B:
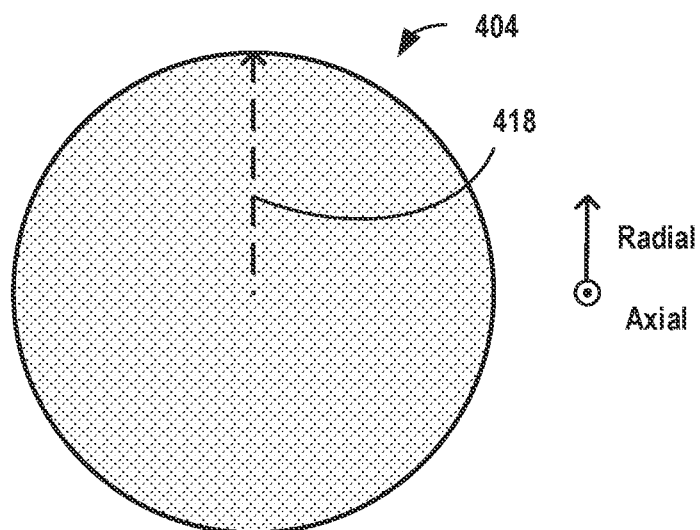
FIG. 4B is a cross-sectional front view diagram illustrating an example fibrous substrate for a pyrolysis reactor having one or more radial gradients.

In some examples, fibrous substrate 404 may operate at one or more radial gradients across axis 410. FIG. 4B is a cross-sectional front view diagram illustrating an example fibrous substrate 404 for pyrolysis reactor 400. Radial gradients 418 may be inherent in a shell-heated design of pyrolysis reactor 400 and/or with the chemistry of the pyrolysis reaction within pyrolysis reactor 400, such that portions of fibrous substrate 404 that are closer to a center of fibrous substrate 404 and/or a center of pyrolysis reactor 400 may have a different temperature or concentration of hydrocarbons or hydrogen gas as portions of fibrous substrate 404 further from a center of fibrous substrate 404 and/or a center of pyrolysis reactor 400. The various radial gradients 418 may cumulatively influence the rate of carbon deposition across axis 410.

In some instances, radial gradient 418 may include a temperature gradient or curve across axis 410. For example, a temperature within fibrous substrate 404 may increase from an outer surface of fibrous substrate 404, such as in contact with a heat source, toward axis 410. As temperature increases, a rate of the endothermic pyrolysis reaction increases, thereby increasing a rate of carbon deposition on fibrous substrates 404. As a result of the various radial gradients 418 on the rate of carbon deposition, a fibrous substrate 404 may accumulate carbon unevenly across axis 410. For fibrous substrates 404 having a uniform density across axis 410, this uneven accumulation may cause a substantial reduction in surface area or residence time at outer radial portions of fibrous substrate 404, leading to replacement of fibrous substrate 404 prior to full or substantially full loading of substrate 404.

In some examples, fibrous substrates 404 may be configured with an initial surface area or density that varies across axis 410, such that fibrous substrates 404 may be configured to passively control a rate of carbon deposition across axis 410. For example, an initial surface area or density of fibrous substrates 404 may be increased in particular radial portions of fibrous substrates 404 that may receive a higher rate of carbon deposition than other portions, such as outer portions of fibrous substrates 404 at a higher temperature. As a result, fibrous substrates 404 may accumulate a greater amount of carbon prior to being replaced compared to a fibrous substrate that does not include a radially varying initial surface area or density.

In some instances, recovery of carbon from pyrolysis of hydrocarbons may be measured or controlled using a concentration of one or more hydrocarbon byproducts or soot precursors produced during pyrolysis as feedback for accumulation of recovered carbon and/or rate of carbon deposition. As explained above, soot may be formed through a progression of one or more hydrocarbon intermediates. For example, during pyrolysis at high temperatures, hydrocarbons such as methane may lose hydrogen to form various two-carbon intermediates, such as acetylene ($C_2H_2$). Acetylene may react with deposition surfaces of fibers to form deposited carbon and/or react in a gas phase to form various derivatives, such as benzene or larger unsaturated hydrocarbons, eventually forming soot. The rates of both the surface reaction of acetylene and the gas phase reaction may be proportional to a concentration of acetylene in the gas phase (and similarly for the various derivatives of acetylene, referred to here as "acetylene" for simplicity). As carbon accumulates on the fibrous substrates and a surface area and/or a void fraction of the fibrous substrates decreases, a rate of the surface reaction of acetylene may decrease and a rate of the gas phase reaction of acetylene may increase. As a result, a concentration of hydrocarbon soot precursors, such as acetylene or its derivatives, may increase as capacity of the fibrous substrates decreases.

Figure 5A:
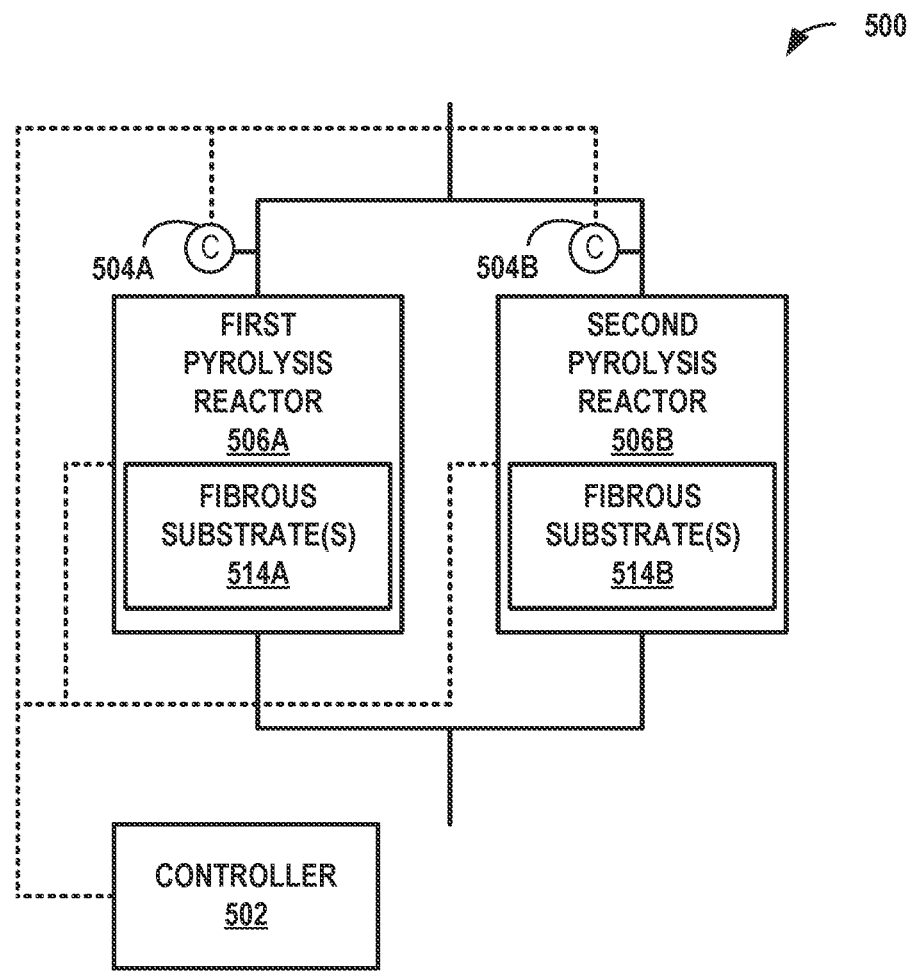
FIG. 5A is a schematic block diagram illustrating an example configuration of multiple pyrolysis reactors for generating hydrogen gas from hydrocarbons.

FIG. 5A is a schematic block diagram illustrating an example pyrolysis system 500 of multiple pyrolysis reactors for generating hydrogen gas from hydrocarbons and measuring a concentration of at least one of a hydrocarbon byproduct or a hydrocarbon soot precursor; however, in other examples, system 500 may include only a single pyrolysis reactor. In the example of FIG. 5A, configuration 500 includes two pyrolysis reactors 506A and 506B (individually "pyrolysis reactor 506" and collectively "pyrolysis reactors 506"), each including one or more fibrous substrates 514A and 514B, respectively. Pyrolysis reactors 506A and 506B include a respective concentration sensor 504A and 504B (individually "concentration sensor 504" and collectively "concentration sensors 504"). Unless otherwise indicated, pyrolysis reactors 506A and 506B, fibrous substrates 514A and 514B, and concentration sensors 504A and 504B may be functionally, structurally, and operationally similar to pyrolysis reactor 200 and fibrous substrates 204 of FIGS. 2A-2C and/or pyrolysis reactor 400, fibrous substrates 404, and concentration sensors 414 of FIGS. 4A and 4B. While illustrated as downstream of pyrolysis reactors 504, each concentration sensor 504 may be positioned at any location within or downstream of pyrolysis reactors 506. Pyrolysis reactors 506 may be arranged in parallel, such that hydrogen generation may be continued while one of pyrolysis reactors 506 is undergoing maintenance. Each concentration sensor 504 may be configured to measure a concentration of at least one of a hydrocarbon byproduct or a hydrocarbon soot precursor of a respective pyrolysis reactor. In some instances, the at least one of the hydrocarbon byproduct or the hydrocarbon soot precursor measured by concentration sensors 504 may include at least one of acetylene or benzene.

In some examples, system 500 includes a controller 502 communicatively coupled to equipment and/or instrumentation of system 500. Controller 502 may include any of a wide range of devices, including processors including processing circuitry (e.g., one or more microprocessors, one or more application specific integrated circuits (ASICs), one or more field programmable gate arrays (FPGAs), or the like), one or more servers, one or more desktop computers, one or more notebook (i.e., laptop) computers, one or more cloud computing clusters, or the like.

In some examples, controller 502 may be communicatively coupled to concentration sensors 504 and configured to receive, from concentration sensors 504, measurements of the concentration of at least one of a hydrocarbon byproduct or a hydrocarbon soot precursor from within or downstream of a respective pyrolysis reactor 506. Controller 502 may be configured to use the concentration of the hydrocarbon byproducts and/or hydrocarbon soot precursors as feedback as to how fibrous substrates 514 are recovering carbon, such as an extent of carbon loading within substrates 514 or a rate of carbon deposition in substrates 514.

Controller 502 may be configured to determine whether a concentration of at least one of a hydrocarbon byproduct or a hydrocarbon soot precursor violates one or more thresholds, such as exceeds a maximum threshold or falls below a minimum threshold. As will be explained further below, the one or more thresholds may correspond to a service life of fibrous substrates 514, an operating setpoint of pyrolysis reactors 506, or any other limit related to carbon loading of fibrous substrates 514 or a rate of carbon deposition within fibrous substrates 514. The one or more thresholds may be an absolute concentration, such as a maximum concentration of a particular hydrocarbon byproduct or hydrocarbon soot precursor like acetylene, or may be a relative concentration of one or more hydrocarbon byproducts or hydrocarbon soot precursors with another gas, such as a ratio of acetylene to benzene (which may indicate a progression toward soot formation) or a ratio of acetylene to methane.

In some instances, controller 502 may be configured to determine and output an indication of an operational state of fibrous substrates 514 of a respective pyrolysis reactor 506. An operational state of fibrous substrates 514 may include any condition of fibrous substrates 514 related to a rate of carbon deposition on fibrous substrates 514, including carbon loading or service life. For example, various concentrations of hydrocarbon precursors may correspond to a particular carbon loading of fibrous substrates 514 within the respective pyrolysis reactor 506, such that exceeding a particular threshold may indicate a loading status (e.g., carbon loading as a percentage) of the fibrous substrates 514 or a service life (e.g., estimated remaining life as a time value) of fibrous substrates 514. In examples in which the threshold represents a service life of the one or more fibrous substrates, controller 502 may be configured to output a maintenance indication, such as a visual or audio indication via a user interface.

In some instances, controller 502 may be configured to determine and output a maintenance action associated with a service life of fibrous substrates 514 of the respective pyrolysis reactor 506. A maintenance action associated with a service life of fibrous substrates 514 may include any action associated with ceasing operation of or replacing fibrous substrates 514. One or more thresholds may represent an absolute service life of fibrous substrates 514, such that violating the thresholds may initiate one or more actions that may assist in replacing fibrous substrates 514 or maintain continuity of operation while the respective pyrolysis reactor 506 is taken offline. Controller 502 may include one or more interlocks or other automatic actions configured to protect a respective pyrolysis reactor 506 or ensure continuity of operation of system 500. In some examples, controller 502 may be configured to initiate a shutdown of the respective pyrolysis reactor 506. For example, controller 502 may be configured to switch operation to another pyrolysis reactor 506, such as operation from first pyrolysis reactor 506A to second pyrolysis reactor 506B (e.g., if second pyrolysis reactor 506B is offline) or modify operation at another pyrolysis reactor 506 (e.g., if both pyrolysis reactors 506 are online).

In some instances, controller 502 may be configured to determine and output a control action associated with one or more operating conditions of the respective pyrolysis reactor 506. A control action associated with one or more operating conditions of the respective pyrolysis reactor 506 may include any action associated with continuing modified operation of pyrolysis reactor 506 with the existing fibrous substrates 514. In some instances, the concentration of at least one of a hydrocarbon byproduct or a hydrocarbon soot precursor may be a variable for which controller 502 may actively control pyrolysis reactors 506 to maintain below a threshold. For example, the concentration of hydrocarbon soot precursors such as acetylene may be correlated with soot formation, such that as the concentration of the various hydrocarbon soot precursors increases, the likelihood of forming soot may correspondingly increase. As such, controller 502 may be configured to actively maintain the concentration of the various hydrocarbon byproducts and/or hydrocarbon soot precursors below one or more thresholds as control setpoints to reduce soot formation. As explained above with respect to pyrolysis reactor 400 of FIGS. 4A and 4B, one or more operating conditions within pyrolysis reactor 506 may influence a rate of carbon deposition on fibrous substrates 514. As one example, due to various axial and/or radial gradients in pyrolysis reactors 506, such as axial gradients 416 and radial gradients 418 described in FIGS. 4A and 4B, carbon may collect in fibrous substrates in different rates along an axis of pyrolysis reactors 506. As another example, due to reduced void fraction resulting from recovered carbon, a residence time of hydrocarbons within fibrous substrates 514 may be reduced as the service life of fibrous substrates 514 progresses.

Controller 502 may be configured to change one or more operating conditions of the respective pyrolysis reactor 506 (or both pyrolysis reactors 506) based on the concentration of the at least one of a hydrocarbon byproduct or a hydrocarbon soot precursor to reduce the concentration of the hydrocarbon soot precursors or maintain the concentration of the hydrocarbon byproducts and/or hydrocarbon soot precursors below the threshold. As one example, controller 502 may be configured to change a temperature profile along an axis of the respective pyrolysis reactor 506 based on the concentration of one or more hydrocarbon byproducts and/or hydrocarbon soot precursors. For example, controller 502 may be configured to increase a temperature of fibrous substrates 514 (or portions of fibrous substrates 514) that may have relatively low carbon loading compared to other fibrous substrates 514, such as fibrous substrates 514 near ends of pyrolysis reactor 506, thereby increasing carbon deposition in those less loaded fibrous substrates 514 and reducing the concentration of the hydrocarbon byproducts and/or hydrocarbon soot precursors. As another example, controller 502 may be configured to change a flow rate of the hydrocarbon into the respective pyrolysis reactor 506 based on the concentration of the one or more hydrocarbon byproducts and/or hydrocarbon soot precursors. For example, controller 502 may be configured to reduce a flow rate into the respective pyrolysis reactor 506 to increase the residence time of the hydrocarbons in fibrous substrates 514 (or portions of fibrous substrates 514) that may have relatively low loading compared to other fibrous substrates 514, such as fibrous substrates 514 near an outlet of pyrolysis reactor 506, thereby increasing carbon deposition in those less loaded fibrous substrates 514 and reducing the concentration of the hydrocarbon soot precursors.

Figure 5B:
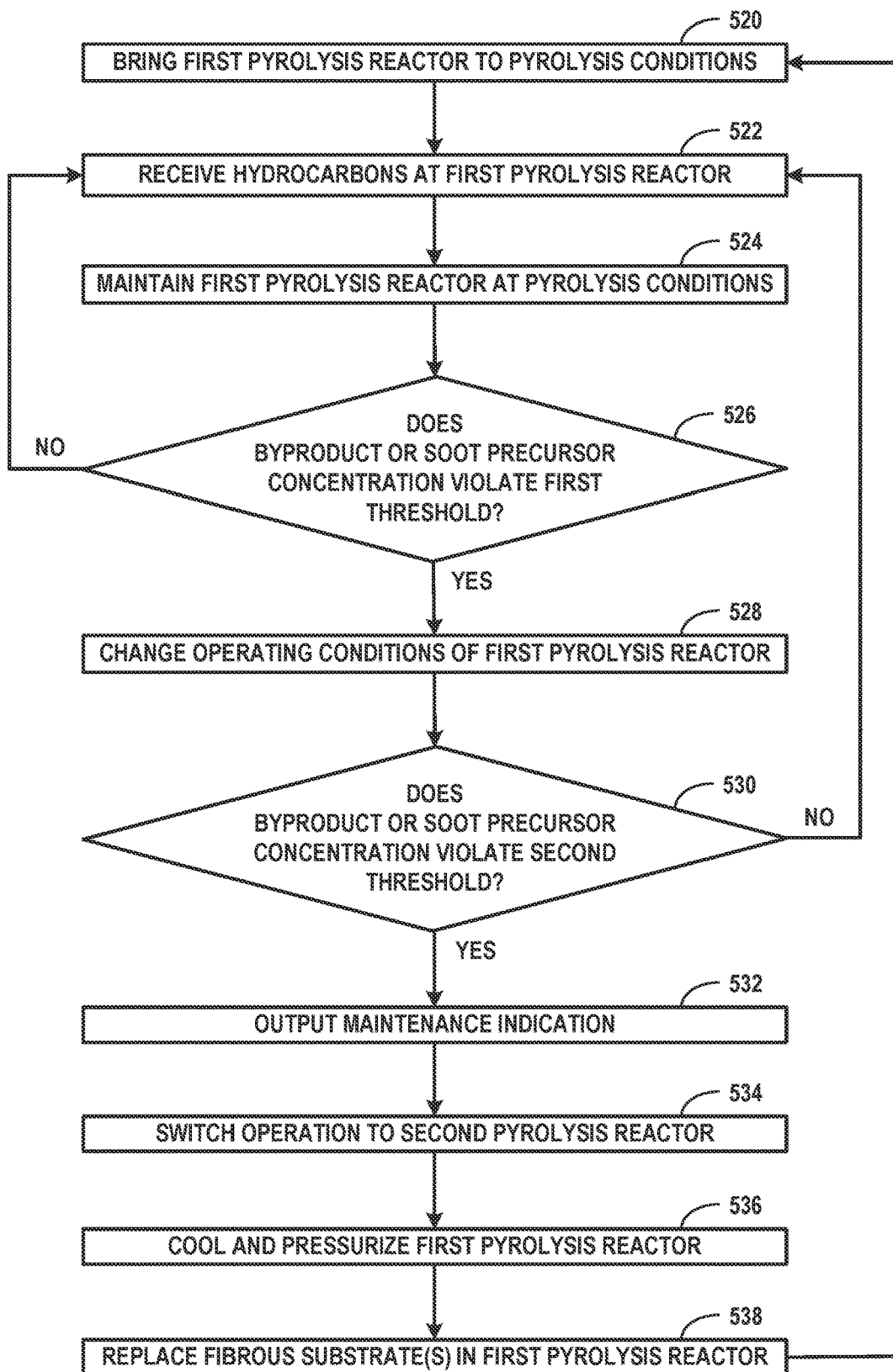
FIG. 5B is a flowchart of an example technique for pyrolyzing hydrocarbons.

FIG. 5B is a flowchart of an example technique for pyrolyzing hydrocarbons. The example technique of FIG. 5B will be described with reference to system 500 of FIG. 5A with operations controlled by controller 502; however, other pyrolysis reactors or configurations of pyrolysis reactors may be used to perform the example technique of FIG. 5B, and certain actions performed by controller 502 may be performed partially or wholly manually (e.g., shutting down a pyrolysis reactor). For example, rather than two pyrolysis reactors operating in parallel, a system implementing the technique of FIG. 5B may include only a single pyrolysis reactor operating on its own or more than two pyrolysis reactors operating according to a regular replacement schedule (e.g., 10 pyrolysis reactors, in which maintenance time represents less than 10% of total operating time for each pyrolysis reactor).

The example technique may include bringing first pyrolysis reactor 506A to pyrolysis conditions (520). For example, controller 502 may send control signals to one or more internal or external heaters of first pyrolysis reactor 506A to heat the pyrolysis chamber to a target temperature, such as temperatures between 850° C. and 1300° C., and preferably between 1050° C. and 1200° C., and/or send control signals to one or more inlet or outlet control valves or a compressor to create a vacuum within the pyrolysis chamber, such as a pressure between 1 kPa and 65 kPa, and preferably between 7 kPa and 30 kPa.

The example technique may include receiving hydrocarbons at first pyrolysis reactor 506 (522). For example, first pyrolysis reactor 506A may receive hydrocarbons that include predominantly methane, such as from a Sabatier reactor or other hydrocarbon source. In the example of FIG. 5B, first pyrolysis reactor 506A may receive a continuous flow of hydrocarbons within a particular batch of fibrous substrates 514.

The example technique may include pyrolyzing the hydrocarbon to generate the hydrogen gas and carbon by maintaining first pyrolysis reactor 506A at pyrolysis conditions (524). Pyrolysis of hydrocarbons is an endothermic reaction, and maintaining a high temperature (e.g., between about 850° C. and about 1300° C.) may result in severing of carbon-carbon bonds and, correspondingly, higher conversion of hydrocarbons to hydrogen gas and carbon. In some examples, maintaining first pyrolysis reactor 506A at the pyrolysis conditions may include controlling a temperature gradient along an axis of first pyrolysis reactor 506A. For example, as discussed in FIGS. 4A and 4B above, a rate of reaction may be influenced by temperature. To control the rate of deposition using temperature, controller 502 may be configured to send control signals to one or more heaters of the pyrolysis reactor to create a temperature gradient along the axis.

The example technique may include measuring, by concentration sensor 504A, a concentration of at least one of a hydrocarbon byproduct or a hydrocarbon soot precursor and determining whether the concentration of the hydrocarbon byproducts and/or hydrocarbon soot precursors violates one or more thresholds corresponding to production of soot (526 and 530). For example, a threshold concentration of acetylene or other hydrocarbon byproducts or hydrocarbon soot precursors may be configured to be concurrent with or prior to production of soot. Concentration sensor 504A in first pyrolysis reactor 506A and/or downstream of first pyrolysis reactor 506A may measure a concentration of one or more hydrocarbon byproducts or hydrocarbon soot precursors and output one or more indications or actions and/or control one or more pyrolysis conditions based on the concentration of at least one of a hydrocarbon byproduct or a hydrocarbon soot precursor. For example, as explained above, production of hydrocarbon soot precursors such as acetylene or benzene may indicate that a surface area within fibrous substrates 514A may not be sufficient to deposit carbon on fibrous substrates 514A.

One or more concentration sensors 504A in first pyrolysis reactor 506A and/or downstream of first pyrolysis reactor 506A may measure a concentration of at least one of a hydrocarbon byproduct or a hydrocarbon soot precursor and send measurement signals to controller 502. As will be described in steps 528, 532, 534, and 536 below, in response to determining that the concentration of at least one of a hydrocarbon byproduct or a hydrocarbon soot precursor violates one or more thresholds, controller 502 may output a variety of actions or indications, such as an operational status of fibrous substrates 514A of first pyrolysis reactor 506A (e.g., step 532), a maintenance action associated with a service life of fibrous substrates 514A of first pyrolysis reactor 506A (e.g., steps 532, 534, 536), or a control action associated with one or more operating conditions of first pyrolysis reactor 506A (e.g., step 528).

The example technique of FIG. 5B may include evaluating the concentration of at least one of a hydrocarbon byproduct or a hydrocarbon soot precursor against two different thresholds—a first threshold and a second threshold—including different hydrocarbon byproducts and/or hydrocarbon soot precursors at different thresholds. The first threshold may be a lower threshold configured as a setpoint for maintaining operating conditions of first pyrolysis reactor 506A. For example, the first threshold may represent an active maximum concentration for controlling first pyrolysis reactor 506A. The second threshold may be a higher threshold configured for indicating or initiating when fibrous substrates 514 may require replacing. For example, the second threshold may represent a maximum concentration corresponding to a service life of fibrous substrates 514. For illustration purposes, the examples technique of FIG. 5B will be described as operating based on both first and second thresholds in series; however, in other examples, only one of the thresholds (or another threshold associated with carbon loading or rate of carbon deposition) may be used, and greater or fewer actions (e.g., steps 528, 532, 534, 536) may be associated with violating particular thresholds.

The example technique may include determining whether the concentration of at least one of a hydrocarbon byproduct or a hydrocarbon soot precursor violates the first threshold corresponding to production of soot (526). For example, the first threshold may be a maximum threshold corresponding to a control point for maintaining a concentration of at least one of a hydrocarbon byproduct or a hydrocarbon soot precursor. In response to determining that the concentration of at least one of a hydrocarbon byproduct or a hydrocarbon soot precursor does not violate the concentration threshold ("NO"), controller 502 may control first pyrolysis reactor 506A to pyrolyze hydrocarbons (522 and 524). For example, controller 502 may determine that the concentration of one or more hydrocarbon byproducts or precursors does not exceed the maximum first threshold and may continue to operate first pyrolysis reactor 506A under the current operating conditions.

In response to determining that the concentration of at least one of a hydrocarbon byproduct or a hydrocarbon soot precursor violates the first threshold ("YES"), controller 502 may take corrective action for first pyrolysis reactor 506 by changing one or more operating conditions within first pyrolysis reactor 506A (528). Controller 502 may change any operating conditions that may decrease a concentration of at least one of a hydrocarbon byproduct or a hydrocarbon soot precursor below (or increase above) the first threshold including, but not limited to, temperature, flow rate, pressure, and the like.

In some examples, controller 502 may change a temperature profile along or across an axis of first pyrolysis reactor 506A based on the concentration of at least one of a hydrocarbon byproduct or a hydrocarbon soot precursor. For example, in examples in which pyrolysis reactors 506 are plug flow reactors, controller 502 may increase the temperature of one or more portions along or across the axis of first pyrolysis reactor 506A, and therefore increase a rate of carbon deposition in the one or more portions.

In some examples, controller 502 may change a flow rate of the hydrocarbon into first pyrolysis reactor 506A based on the concentration of at least one of a hydrocarbon byproduct or a hydrocarbon soot precursor. For example, controller 502 may reduce the flow rate of hydrocarbons to first pyrolysis reactor 506A, and therefore increase a residence time of hydrocarbons in pyrolysis reactor 506A, including in particular fibrous substrates 514 that may have lower loading. In some instances, controller 502 may perform load balancing between pyrolysis reactors 506. For example, controller 502 may control first pyrolysis reactor 506A to reduce a flow rate, and therefore residence time, of hydrocarbons to first pyrolysis reactor 506A and increase a flow rate of hydrocarbons to second pyrolysis reactor 506B that may have a lower concentration of acetylene or other hydrocarbon soot precursors.

The example technique may include determining whether the concentration of at least one of a hydrocarbon byproduct or a hydrocarbon soot precursor violates the second threshold corresponding to a service life of fibrous substrates 514A (530). For example, the second threshold may be a maximum threshold or schedule of thresholds of concentrations of hydrocarbon byproducts or hydrocarbon soot precursors that correspond to a particular service life of fibrous substrates 514A, such as a maximum service life or a percentage or fraction of service life (such as may be determined experimentally or according to a model or simulation). In response to determining that the concentration of the hydrocarbon byproducts and/or hydrocarbon soot precursors does not violate the second threshold ("NO"), first pyrolysis reactor 506A may continue to pyrolyze hydrocarbons (522 and 524). For example, controller 502 may determine that the concentration of one or more hydrocarbon byproducts or precursors does not exceed the maximum second threshold and may continue to operate first pyrolysis reactor 506A under the current operating conditions.

In response to determining that the concentration of at least one of a hydrocarbon byproduct or a hydrocarbon soot precursor violates the second threshold ("YES"), controller 502 may take corrective action by outputting an operational status of fibrous substrates 514A and/or outputting a maintenance action associated with a service life of fibrous substrates 514A. In the example of FIG. 5B, controller 502 may output a maintenance indication that one or more fibrous substrates may be replaced (532). In some examples, the maintenance indication may include an indication that alerts an operator as to the operational status of fibrous substrates 514A. For example, the maintenance indication may include an indication of the concentration of at least one of a hydrocarbon byproduct or a hydrocarbon soot precursor, an indication of the remaining service life of fibrous substrates, an indication of an extent of carbon loading of fibrous substrates 514A, or the like.

Further in response to determining that the concentration of at least one of a hydrocarbon byproduct or a hydrocarbon soot precursor violates the second threshold, controller 502 may take corrective action by initiating a shutdown of first pyrolysis reactor 506A. In some examples, shutting down first pyrolysis reactor 506A may include first switching or offloading operation to second pyrolysis reactor 506B (540). For example, controller 502 may output an indication that one or more fibrous substrates 514A in first pyrolysis reactor 506A requires replacing and send control signals to a control valve to divert flow of hydrocarbons from first pyrolysis reactor 506A to second pyrolysis reactor 506B. The example technique may include cooling down and pressurizing the first pyrolysis reactor (536) to conditions safe for accessing the pyrolysis chamber, such as a temperature and/or pressure of an ambient environment.

The example technique of FIG. 5B may include replacing one or more fibrous substrates in the first pyrolysis reactor (538) by removing the loaded fibrous substrates 514A and inserting unloaded fibrous substrates. Once the unloaded fibrous substrates have been inserted into first pyrolysis reactor 506A, first pyrolysis reactor 506A may be brought back online (500), such as in parallel with second pyrolysis reactor 506B or once another pyrolysis reactor (not shown) is brought offline.

EXPERIMENTAL EXAMPLES

Methane pyrolysis may achieve a high oxygen recovery for an overall system in Environmental Control and Life Support Systems (ECLSS) of spacecraft. This high oxygen recovery may be inherent in the chemistry of methane pyrolysis, as elemental carbon is the only carbon-containing product. Methane pyrolysis may be simple and direct, and the carbon generated as a byproduct may find uses in future missions. Since this carbon is mechanically strong and non-sooty, it may be well-suited for space applications where contamination by dust or soot must be avoided. As will be illustrated experimental below, fibrous substrates used for carbon deposition may have sufficient surface area to avoid or substantially reduce soot generation while reducing initial density.

Experimental Results for Different Substrate Materials and Structures

Experimental investigations were carried out in a small-scale reactor set-up comprising a high-temperature tube furnace, flow controllers, a vacuum pump, and a pressure control system. Substrates were positioned in the reactor tube either on a quartz rod or supported by the reactor wall if the material was not self-supporting. Temperatures, pressure, and flow rates were continually monitored, and an on-line mass spectrometer allowed continuous monitoring of the gas phase composition. Periodic samples were removed and analyzed by gas chromatography. Upon completion of a run, the weight of the product parts was compared with that of the initial substrates.

This procedure was used to study the performance of carbon fiber, quartz fiber, and porous structured zirconia substrates as possible substrate materials for the methane pyrolysis CVD reaction. Carbon fiber substrates were acquired as unidirectional carbon fiber plies felted together and die cut into discs. Coarse quartz fiber could not be formed into discs, so therefore was obtained as quartz wool. Porous structured zirconia with 30 pores per inch (ppi) was cut into discs using a ceramic saw. Additional substrate characteristics, such as relative surface area, are noted in Table 1 below, normalized to the carbon fiber substrate for comparison.

TABLE 1

Characteristics of Substrate Materials

| Property | Carbon Fiber | Quartz Wool | Porous Zirconia |
|---|---|---|---|
| Void Fraction (%) | 60-80 | ~98 | 85 |
| Density (g/cm$^3$) | 0.4-0.75 | ~0.03 | 0.9 |
| Relative Surface Area | 1.0 | ~0.04 | 0.01 |
| Max. Operable Temperature (° C.) | >2500 | 1050 | 1650 |

The substrates were placed in the reactor and run in a flow of pure methane. The carbon fiber discs and zirconia discs were supported on a quartz rod about 5 mm from the reactor wall, while the quartz wool was stuffed to fill the reactor tube against the walls. Each run used only one type of substrate material in order to test the effects of pore structure, material, mass transfer effects (resulting from open porosity and pathways around the substrate), and surface area.

TABLE 2

Experimental Results Using Substrate Materials

| Measurement | Carbon Fiber | Quartz Wool | Porous Zirconia | No Substrate |
|---|---|---|---|---|
| Ave. Dep. Rate (g/cm$^2$ · hr) | $1.0 \times 10^{-6}$ | $5.5 \times 10^{-6}$ | $9.1 \times 10^{-6}$ | N/A |
| Initial C$_2$H$_2$ Concentration (normalized) | 0.11 | 0.70 | 0.63 | 1 |
| CVD Carbon Select. (%) | 100 | 100* | 91 | 57 |

For all substrates and a run in which no substrates were placed in the reactor, the conversion remained consistent within 5%, indicating that temperature, pressure, and residence time determine conversion. Table 2 shows additional results from these experiments, showing that the substrate surface area instead affects the reaction partitioning. This is illustrated in the CVD carbon selectivity results. CVD carbon selectivity is calculated as the percentage of converted carbon in the feed stream that is captured as the desired deposited carbon on the substrates after the completion of a run. A value less than 100% indicates that carbon was lost to the process as soot or other high molecular weight carbon compounds. The empty reactor with no substrate surface area had a low mass balance of 57% and produced soot immediately during the run, correlating to the highest initial acetylene production (first measurement of acetylene after lining out). Soot formation was also observed for the porous zirconia substrate, which had relatively low surface area compared to the fibrous substrates. While the quartz wool substrate is shown with >99% CVD carbon selectivity, the high acetylene production and lower surface area suggest that it is possible that some soot was present but entrapped by the substrate. This material became very brittle after use, was difficult to remove from the reactor walls, and carbon dust resulted from handling.

These results indicated that carbon fiber material may be a good candidate for substrates in the methane pyrolysis process due at least to the high temperature stability and ability to manufacture into high-surface area, self-supporting substrates that promote high selectivity to CVD carbon.

Experimental Results for Different Carbon Fiber Densities

To increase maintenance interval and reduce consumable mass, the design of the carbon fiber substrates may be improved through design of various properties of the fibrous substrates, as discussed above. While the high relative surface area of the baseline carbon fiber material resulted in excellent partitioning towards CVD carbon, the resulting higher material density and lower loading capacity resulted in less than desirable equivalent system mass (ESM) trades. ESM may be a quantification of a contribution of mass, volume, power, cooling, and other factors. Experiments were completed using similar carbon fibers, but with increased void fraction and corresponding reduced density, and therefore reduced surface area (although still comparably higher than the quartz wool or porous zirconia). Substrates with densities of 0.3 g/cm$^3$ and 0.14 g/cm$^3$ were obtained. The objective of the study was to understand the effect of reduced substrate density and surface area on methane conversion and soot generation during an extended run. Table 3 summarizes the characteristics of these carbon fiber substrates as well as the results of the runs.

TABLE 3

Characteristics of Carbon Fiber Substrate Materials

| Property | Baseline | Woven | Felt |
| --- | --- | --- | --- |
| VoidFraction (%) | 60-80 | 85 | 91 |
| Density (g/cm$^3$) | 0.4-0.75 | 0.3 | 0.14 |
| Relative Surface Area | 1.0 | 0.6 | 0.28 |

Figure 6A:
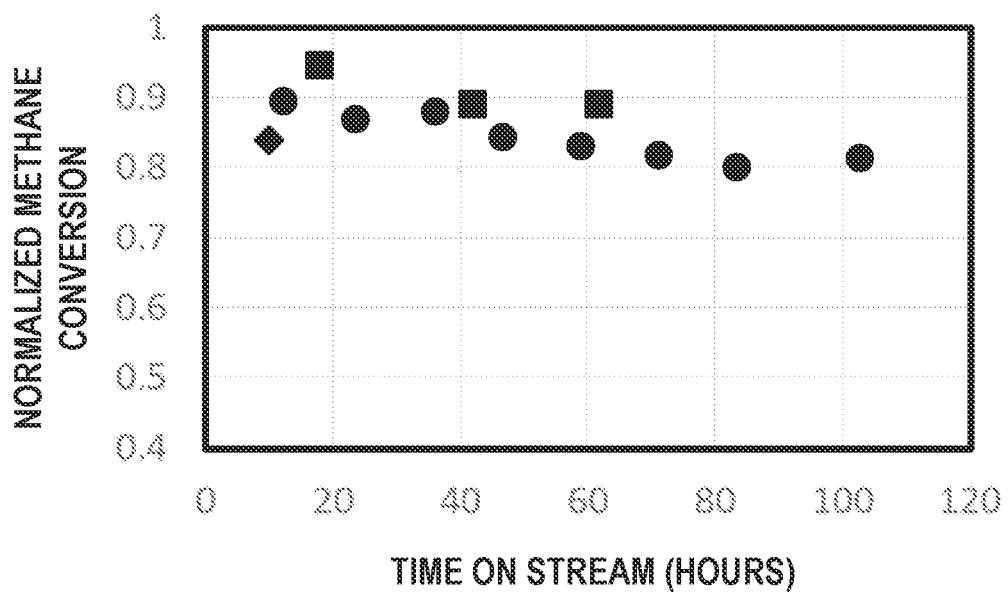
FIG. 6A is a graph of methane conversion over time for an experimental pyrolysis reactor using different densities of carbon fiber substrate materials.
Figure 6B:
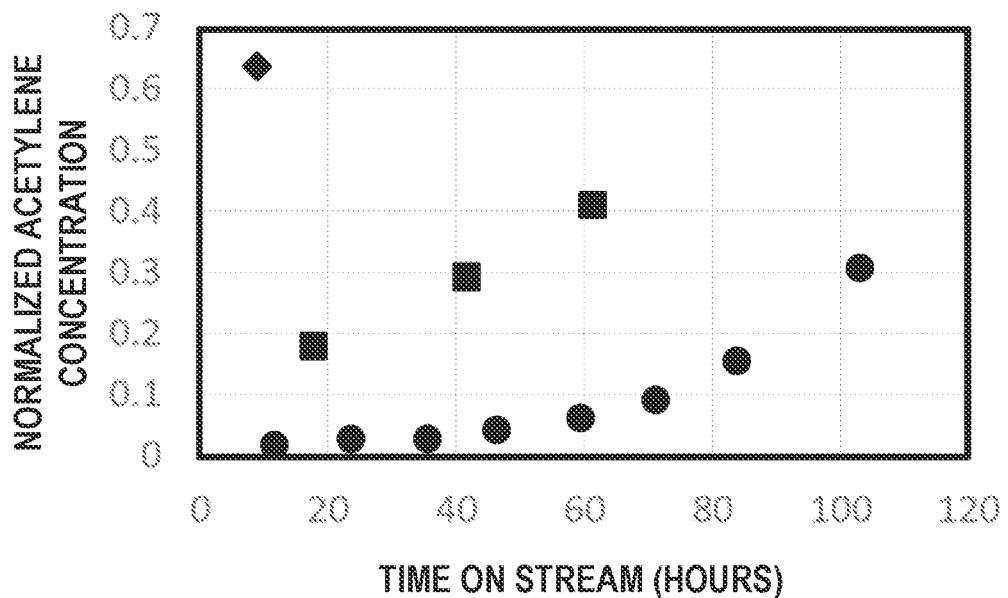
FIG. 6B is a graph of acetylene concentration over time for an experimental pyrolysis reactor using different densities of carbon fiber substrate materials.

FIG. 6A is a graph of methane conversion over time for an experimental pyrolysis reactor using different densities of carbon fiber substrate materials, while FIG. 6B is a graph of acetylene concentration over time for an experimental pyrolysis reactor using different densities of carbon fiber substrate materials, including baseline substrate (circle), woven substrate (square), and felt substrate (triangle). FIGS. 6A and 6B illustrate methane conversion, calculated from the methane concentration, and acetylene concentration as a function of time on stream, respectively. Methane conversion, as expected, was largely insensitive to the reduction in surface area, and slowly declined over the course of each run. Without being limited to any particular theory, this decline may be due to a reduction in the reactor volume as it fills with carbon and therefore the reduction in residence time in the reactor. In contrast, initial acetylene concentrations increased with decreasing substrate surface area, and the rate of increase in the acetylene concentration with time on stream also increased. No soot generation was observed for the baseline substrates until roughly 110 hours, but soot was observed at less than 60 hours when the 0.3 g/cm$^3$ substrates were used. The experiment using 0.14 g/cm$^3$ substrates was terminated after the first measurement due to excessive soot generation. These results correlated to the measured acetylene production.

TABLE 4

Experimental Results of Carbon Fiber Substrates Materials

| Measurement | Baseline | Woven | Felt |
| --- | --- | --- | --- |
| Initial C$_2$H$_2$ Concentration (normalized) | 0.01 | 0.19 | 0.64 |
| Operation Before Soot Observation (hrs) | 110 | 60 | 9 |

As described above, there is a strong incentive to reduce an initial density of fibrous substrates to increase capacity and decrease the number of substrates required for a long mission. However, reducing density in a way that also reduces surface area may lead to higher acetylene concentrations and premature generation of soot. Because soot generation is undesirable in space, and maintenance intervals must be chosen to avoid it, any benefit from the lower density substrates may not be realized due to the limited maintenance interval. Other parameters that affect acetylene concentration include temperature, pressure, and residence time. Improvement of these parameters may reduce initial density without causing the problems described above, and may result in substrate design in which porosity can be increased without decreasing surface area.

To understand the effect of surface area, a series of experiments were performed at reactor conditions of 1165° C. and 100 torr pressure in which the inlet flowrate of methane was systematically varied to vary the residence time in the reactor. The ratio of surface area of fibrous substrate to volume of fibrous substrate (SA/V) was changed by varying the dimensions and/or the initial density of the fibrous substrates, and was estimated from the fiber diameter of the fibrous substrates, the weight of the fibrous substrates, and the volume of the reactor. Since these experiments were short, insufficient carbon build up occurred to change the surface area/volume ratio from the initial value. The gas phase composition was analyzed by gas chromatography at each flow rate.

Figure 7A:
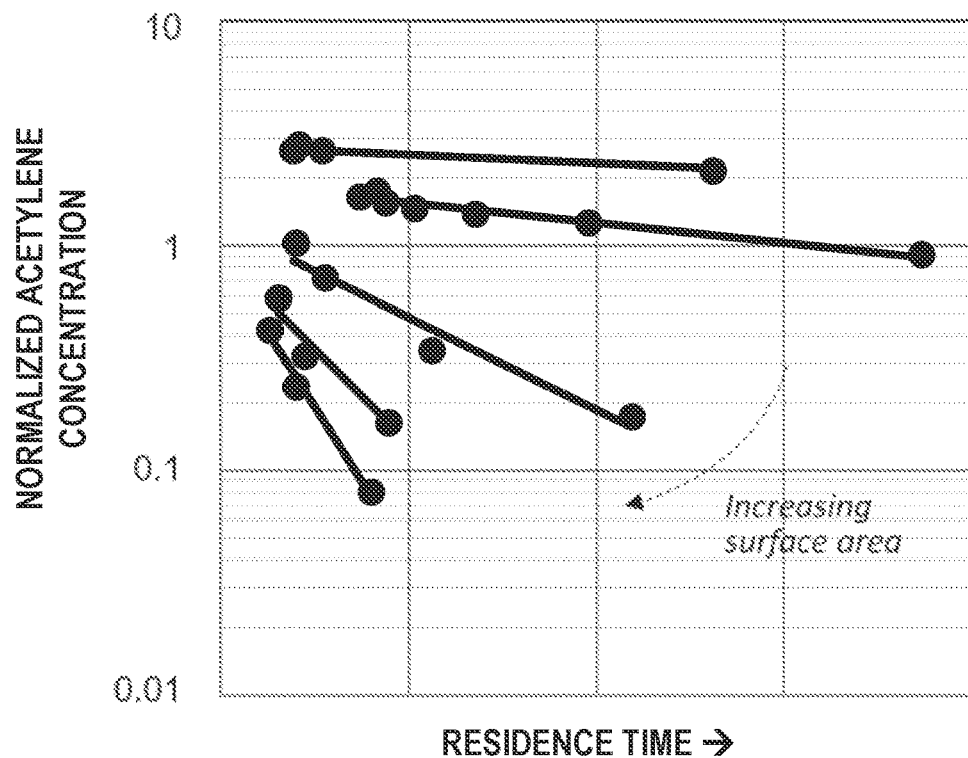
FIG. 7A is a graph of acetylene concentration with increasing residence time for an experimental pyrolysis reactor using different densities of carbon fiber substrate materials.
Figure 7B:
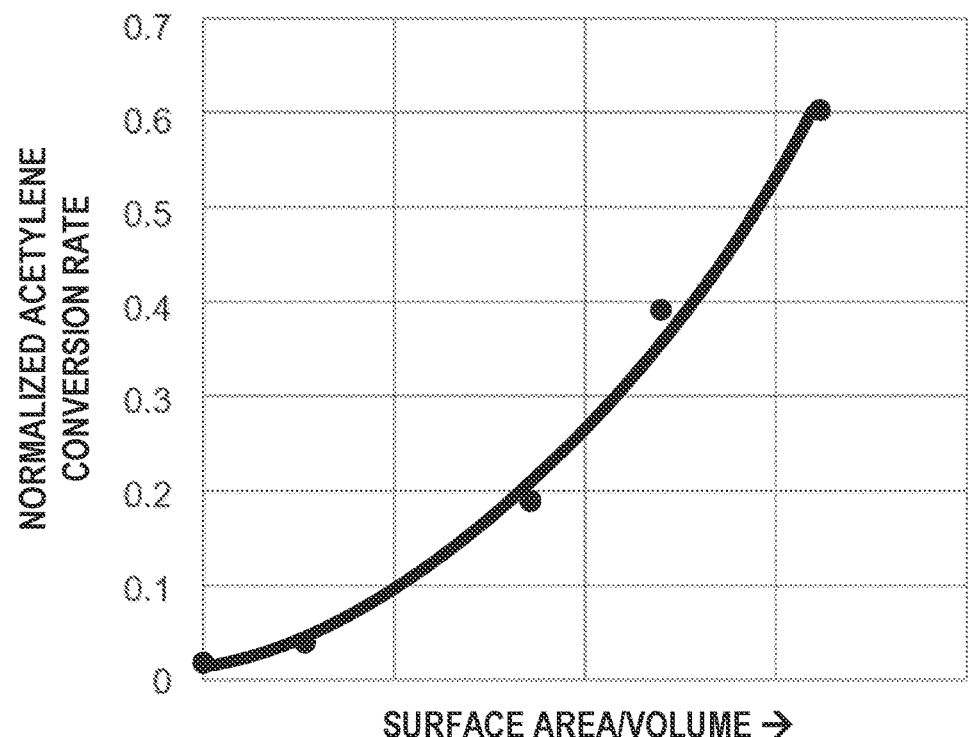
FIG. 7B is a graph of acetylene conversion rate with increasing surface area to volume for an experimental pyrolysis reactor having different densities of carbon fiber substrate materials.

FIG. 7A is a graph of acetylene concentration with increasing residence time for an experimental pyrolysis reactor using different densities of carbon fiber substrate materials, while FIG. 7B is a graph of acetylene conversion rate with increasing surface area to volume for an experimental pyrolysis reactor having different densities of carbon fiber substrate materials. Regarding FIG. 7A, a linear fit is observed for each experiment consistent with reaction kinetics that are first order in acetylene concentration. The slope of each curve is the apparent first order rate constant, and these rate constants vary in a consistent way with SA/V, as shown in FIG. 7B, in which these apparent first order rate constants are plotted against it. These results are consistent with the mechanism described above, in which methane decomposes first to acetylene, followed by benzene and other higher molecular weight intermediates until soot forms. When no substrates were present (SA/V=0), the rate of acetylene conversion is low, since only the homogeneous reaction path is available. Under these conditions the acetylene concentration is high, and soot is observed. As SA/V increases, the CVD reaction accelerates, decreasing the steady state acetylene concentration, and reducing the potential for soot formation. Experimentally, no soot was observed for these reactions.

With this relationship in place, more detailed design for the substrate is possible. As described above, the SA/V of the substrate must be kept high enough to prevent soot generation, but within this constraint, there may be a benefit to reducing initial density to maximize loading and therefore maintenance interval. As illustrated above with respect to FIGS. 2B and 2C, the SA/V during pyrolysis may at first increase, as fiber dimensions are increased by carbon deposition, but then will decrease as carbon fills the voids between adjacent fibers, preventing access by the feed. When the SA/V decreases enough that the acetylene concentration rises too high, then the run may be terminated to avoid soot generation. To increase SA/V, the substrates may include fibers having a variety of shapes and sizes configured to increase the surface area of fiber for a particular volume or mass of fibrous substrate. For example, the fibers may have a smaller diameter for an equivalent volume of solid fiber, such as illustrated in FIG. 3A; the fibers may have a lumen or other hollow structure for an equivalent surface area, such as illustrated in FIG. 3B; the fibers may have a surface treatment to increase a surface area for an equivalent volume of solid fiber, such as illustrated in FIG. 3C; and/or the fibers may have a complex shape for an equivalent volume of solid fiber, such as illustrated in FIG. 3D.

Equivalent System Mass

Improvements in the design of the substrates may translate directly into reduction in the equivalent system mass for these consumables. By increasing the porosity of the substrates, not only is the density of the material reduced, corresponding to lower mass, but the loading capacity is increased, allowing for longer maintenance intervals and fewer required substrates overall. The volumetric capacity $C_v$ may be a simple function of the initial and final densities of the substrates, given a material type. The maintenance interval may be the length of time the reactor can operate before the substrates have reached the final density, and is an important parameter for determining ESM. This length of time may be determined by the volumetric capacity of the reactor, the volume of substrates that can fit in the reactor, and the load of carbon generated from the carbon dioxide from the crew. For a crew of four people, an average carbon dioxide generation rate may be about 4.18 kg/day, and if all of that is converted to methane, and then to carbon, would generate 1.1 kg/day of carbon. For a mission length of 1000 days, the number of substrate cartridges required may be calculated. The weight and volume for the number of substrates required may be used to calculate the ESM for the load of consumable substrates. To calculate the weight, the volume of substrates and the initial density may be multiplied by a factor of 1.1, for example, to account for a hardware to support the substrates in the reactor. The substrates, in the current design, fit a cylindrical reactor. The volume is multiplied by a factor to provide the volume occupied by cylinders in a hexagonal close-packed array and by a factor to account for empty spaces between individual substrates. Improvements in the substrates can have a significant effect on their ESM. ESM is calculated as the sum of the weight and the volume-equivalent weight using 35.1 kg m$^{-3}$, for example.

Figure 8:
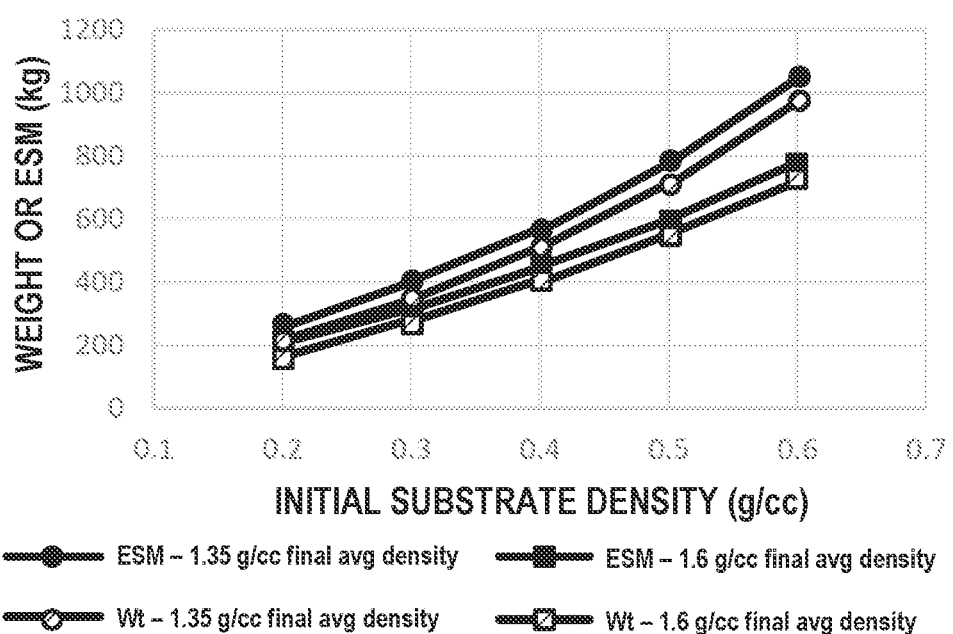
FIG. 8 is a graph of initial and final weights of fibrous substrates for an experimental pyrolysis reactor having different initial densities of carbon fiber substrate materials.

FIG. 8 is a graph of initial and final weights of fibrous substrates for an experimental pyrolysis reactor having different initial densities of carbon fiber substrate materials. FIG. 8 illustrates how varying an initial and final average density of a carbon fiber substrate affects the weight and ESM for a 1000-day supply. Decreasing the initial density and increasing the final average density reduce the ESM. Decreasing the initial density requires finding the balance between porosity and surface area. To increase the final average density, adjustment of the reactor shape and temperature profile is required, so that carbon is spread as evenly as possible across the substrates, increasing the maintenance interval.

Example 1: A system for generating hydrogen includes a pyrolysis reactor configured to generate hydrogen gas from a hydrocarbon through pyrolysis, wherein the pyrolysis reactor comprises one or more fibrous substrates defining a deposition surface for carbon generated from the pyrolysis of the hydrocarbon, wherein each fibrous substrate of the one or more fibrous substrates has an effective void fraction between 40% and 95%, and wherein each fibrous substrate of the one or more fibrous substrates comprises a plurality of fibers configured to maintain chemical and structural stability between 850° C. and 1300° C.

Example 2: The system of example 1, wherein the plurality of fibers has an average fiber diameter that is less than about 10 microns.

Example 3: The system of any of examples 1 and 2, wherein respective fibers of the plurality of fibers each have a non-circular cross-section.

Example 4: The system of example 3, wherein respective fibers of the plurality of fibers have a perimeter that includes at least one of a serrated shape or a multi-lobal shape.

Example 5: The system of any of examples 1 through 4, wherein respective fibers of the plurality of fibers are hollow.

Example 6: The system of any of examples 1 through 5, wherein the pyrolysis reactor defines an inlet at a first end, an outlet at a second end, and an axis between the first and second ends, and wherein the one or more fibrous substrates have a surface area that varies axially along the axis from the inlet to the outlet.

Example 7: The system of any of examples 1 through 6, wherein the pyrolysis reactor defines an inlet at a first end, an outlet at a second end, and an axis between the first and second ends, and wherein the one or more fibrous substrates have a surface area that varies radially along the axis from the inlet to the outlet.

Example 8: The system of any of examples 1 through 7, wherein pyrolysis reactor defines an inlet at a first end, an outlet at a second end, and an axis between the first and second ends, and wherein the pyrolysis reactor is configured to heat at least one fibrous substrate such that the pyrolysis reactor has a temperature that varies axially along the axis from the inlet to the outlet.

Example 9: The system of any of examples 1 through 8, wherein the plurality of fibers comprises at least one of carbon, zirconium dioxide, or silicon dioxide.

Example 10: The system of any of examples 1 through 9, wherein the one or more fibrous substrates are self-supporting.

Example 11: The system of any of examples 1 through 10, wherein the hydrocarbon is methane, wherein the pyrolysis reactor is configured to generate carbon and a first portion of hydrogen gas from the methane, and wherein the system further comprises: a Sabatier reactor configured to: receive the first portion of hydrogen gas from the pyrolysis reactor and a second portion of hydrogen gas from an oxygen generation system; generate the methane and water from carbon dioxide and the first and second portions of hydrogen gas; and discharge the methane to the pyrolysis reactor; and an oxygen generation system configured to: receive the water from the Sabatier reactor; generate oxygen and the second portion of hydrogen gas from the water; and discharge the second portion of hydrogen gas to the Sabatier reactor.

Example 12: A method for generating hydrogen gas includes receiving, by a pyrolysis reactor, a hydrocarbon;

and pyrolyzing, by the pyrolysis reactor, the hydrocarbon to generate the hydrogen gas and carbon, wherein the pyrolysis reactor comprises one or more fibrous substrates defining a deposition surface for the carbon generated from the pyrolysis of the hydrocarbon, wherein each fibrous substrate of the one or more fibrous substrates has an effective void fraction between 40% and 95%, and wherein each fibrous substrate of the one or more fibrous substrates comprises a plurality of fibers configured to maintain chemical and structural stability between 850° C. and 1300° C.

Example 13: The method of example 12, wherein the plurality of fibers has an average fiber diameter that is less than about 10 microns.

Example 14: The method of any of examples 12 and 13, wherein the respective fibers of the plurality of fibers have a non-circular cross-section.

Example 15: The method of example 14, wherein the respective fibers of the plurality of fibers have a perimeter that includes at least one of a serrated shape or a multi-lobal shape.

Example 16: The method of any of examples 12 through 15, wherein the respective fibers of the plurality of fibers have a hollow lumen.

Example 17: The method of any of examples 12 through 16, wherein the pyrolysis reactor defines an inlet at a first end, an outlet at a second end, and an axis between the first and second ends, and wherein the one or more fibrous substrates have a surface area that varies axially along the axis from the inlet to the outlet.

Example 18: The method of any of examples 12 through 17, wherein the pyrolysis reactor defines an inlet at a first end, an outlet at a second end, and an axis between the first and second ends, and wherein the one or more fibrous substrates have a surface area that varies radially across the axis from the inlet to the outlet.

Example 19: The method of any of examples 12 through 18, wherein the pyrolysis reactor defines an inlet at a first end, an outlet at a second end, and an axis between the first and second ends, and wherein heating the hydrocarbon further comprises heating the pyrolysis reactor such that the pyrolysis reactor has a temperature that varies axially along the axis from the inlet to the outlet.

Example 20: The method of any of examples 12 through 19, further includes generating, by the pyrolysis reactor, hydrogen gas and carbon from methane; generating, by a Sabatier reactor, methane and water from carbon dioxide and the hydrogen gas from the pyrolysis reactor; discharging, by the Sabatier reactor, the methane to the methane pyrolysis reactor. generating, by an electrolysis system, oxygen gas and hydrogen gas from the water from the Sabatier reactor; and discharging, by the electrolysis system, the hydrogen gas to the Sabatier reactor.

Example 21: A system for generating hydrogen gas includes one or more pyrolysis reactors configured to generate the hydrogen gas from a hydrocarbon through pyrolysis, wherein each pyrolysis reactor of the one or more pyrolysis reactors comprises: one or more fibrous substrates defining a deposition surface for carbon generated from the pyrolysis of the hydrocarbon, wherein each fibrous substrate of the one or more fibrous substrates comprises a plurality of fibers configured to maintain chemical and structural stability between 850° C. and 1300° C.; and a concentration sensor downstream of at least one fibrous substrate of the one or more fibrous substrates, wherein the concentration sensor is configured to measure a concentration of at least one of a hydrocarbon byproduct or a hydrocarbon soot precursor.

Example 22: The system of example 21, wherein the at least one of the hydrocarbon byproduct or the hydrocarbon soot precursor measured by the concentration sensor comprises at least one of acetylene or benzene.

Example 23: The system of any of examples 21 and 22, further includes receive, from the concentration sensor, a measurement of the concentration of the at least one of the hydrocarbon byproduct or the hydrocarbon soot precursor; and output, in response to determining that the concentration of the at least one of the hydrocarbon byproduct or the hydrocarbon soot precursor violates a threshold, at least one of: an operational status of the fibrous substrates of the respective pyrolysis reactor of the one or more pyrolysis reactors; a maintenance action associated with a service life of the fibrous substrates of the respective pyrolysis reactor of the one or more pyrolysis reactors; or a control action associated with one or more operating conditions of the respective pyrolysis reactor of the one or more pyrolysis reactors.

Example 24: The system of any of examples 21 through 23, wherein the threshold represents an end-of-life of the one or more fibrous substrates, and further comprising a controller configured to output, in response to determining that the concentration of the at least one of the hydrocarbon byproduct or the hydrocarbon soot precursor violates the threshold, a maintenance indication.

Example 25: The system of any of examples 21 through 24, further comprising a controller configured to initiate, in response to determining that the concentration of the at least one of the hydrocarbon byproduct or the hydrocarbon soot precursor violates the threshold, a shutdown of the respective pyrolysis reactor of the one or more pyrolysis reactors.

Example 26: The system of any of examples 21 through 25, further comprising a controller configured to change a temperature profile along an axis of the respective pyrolysis reactor of the one or more pyrolysis reactors based on the concentration of the at least one of the hydrocarbon byproduct or the hydrocarbon soot precursor.

Example 27: The system of any of examples 21 through 26, further comprising a controller configured to change a flow rate of the hydrocarbon into the respective pyrolysis reactor of the one or more pyrolysis reactors based on the concentration of the at least one of the hydrocarbon byproduct or the hydrocarbon soot precursor.

Example 28: The system of any of examples 21 through 27, wherein the one or more pyrolysis reactors comprise a first pyrolysis reactor that includes a first concentration sensor and a second pyrolysis reactor that includes a second concentration sensor, wherein the first and second pyrolysis reactors are coupled in parallel.

Example 29: The system of example 28, further includes receive, from the first concentration sensor, a measurement of the concentration of the at least one of the hydrocarbon byproduct or the hydrocarbon soot precursor from the first pyrolysis reactor; and initiate, in response to determining that the concentration of the one or more hydrocarbon byproducts or soot precursors violates a threshold, a shutdown of the first pyrolysis reactor.

Example 30: The system of any of examples 21 through 29, wherein each fibrous substrate of the one or more fibrous substrates has an effective void fraction between 40% and 95%.

Example 31: A method for generating hydrogen gas includes pyrolyzing, by one or more pyrolysis reactors, a hydrocarbon to generate the hydrogen gas and carbon, wherein each pyrolysis reactor of the one or more pyrolysis reactors comprises one or more fibrous substrates defining a deposition surface for the carbon generated from the pyrolysis of the hydrocarbon, and wherein each fibrous substrate of the one or more fibrous substrates comprises a plurality of fibers configured to maintain chemical and structural stability between about 850° C. and about 1300° C.

Example 32: The method of example 31, wherein the at least one of the hydrocarbon byproduct or the hydrocarbon soot precursor measured by the concentration sensor comprises at least one of acetylene or benzene.

Example 33: The method of any of examples 31 and 32, further includes receiving, by a controller and from the concentration sensor, a measurement of the concentration of the at least one of the hydrocarbon byproduct or the hydrocarbon soot precursor; and outputting, by the controller and in response to determining that the concentration of the at least one of the hydrocarbon byproduct or the hydrocarbon soot precursor violates a threshold, at least one of: an operational status of the fibrous substrates of the respective pyrolysis reactor; a maintenance action associated with a service life of the fibrous substrates of the respective pyrolysis reactor; or a control action associated with one or more operating conditions of the respective pyrolysis reactor.

Example 34: The method of any of examples 31 through 33, wherein the threshold represents an end-of-life of the one or more fibrous substrates, and wherein the method further comprises outputting, by a controller and in response to determining that the concentration of the at least one of the hydrocarbon byproduct or the hydrocarbon soot precursor violates the threshold, a maintenance indication.

Example 35: The method of any of examples 31 through 34, further comprising initiating, by a controller and in response to determining that the concentration of the at least one of the hydrocarbon byproduct or the hydrocarbon soot precursor violates the threshold, a shutdown of the pyrolysis reactor.

Example 36: The method of any of examples 31 through 35, further comprising changing, by a controller, a temperature profile along an axis of the pyrolysis reactor based on the concentration of the at least one of the hydrocarbon byproduct or the hydrocarbon soot precursor.

Example 37: The method of any of examples 31 through 36, further comprising changing, by a controller, a flow rate of the hydrocarbon into the pyrolysis reactor based on the concentration of the at least one of the hydrocarbon byproduct or the hydrocarbon soot precursor.

Example 38: The method of any of examples 31 through 37, wherein the one or more pyrolysis reactors comprise a first pyrolysis reactor that includes a first concentration sensor and a second pyrolysis reactor that includes a second concentration sensor, wherein the first and second pyrolysis reactors are coupled in parallel.

Example 39: The method of example 38, further includes receiving, by a controller and from the first concentration sensor, a measurement of the concentration of the at least one of the hydrocarbon byproduct or the hydrocarbon soot precursor from the first pyrolysis reactor; initiating, by the controller and in response to determining that the concentration of the at least one of the hydrocarbon byproduct or the hydrocarbon soot precursor violates the threshold, a shutdown of the first pyrolysis reactor.

Example 40: The method of any of examples 31 through 39, wherein each fibrous substrate of the one or more fibrous substrates has an effective void fraction between 40% and 95%.

Various examples have been described. These and other examples are within the scope of the following claims.

What is claimed is:

1. A system for generating hydrogen gas, comprising:
one or more pyrolysis reactors configured to generate the hydrogen gas from a hydrocarbon through pyrolysis, wherein each pyrolysis reactor of the one or more pyrolysis reactors comprises:
one or more fibrous substrates defining a deposition surface for carbon generated from the pyrolysis of the hydrocarbon, wherein each fibrous substrate of the one or more fibrous substrates comprises a plurality of fibers configured to maintain chemical and structural stability between 850° C. and 1300° C.; and
a concentration sensor downstream of at least one fibrous substrate of the one or more fibrous substrates, wherein the concentration sensor is configured to measure a concentration of at least one of a hydrocarbon byproduct or a hydrocarbon soot precursor.

2. The system of claim 1, wherein the at least one of the hydrocarbon byproduct or the hydrocarbon soot precursor measured by the concentration sensor comprises at least one of acetylene or benzene.

3. The system of claim 1, further comprising a controller configured to:
receive, from the concentration sensor, a measurement of the concentration of the at least one of the hydrocarbon byproduct or the hydrocarbon soot precursor; and
output, in response to determining that the concentration of the at least one of the hydrocarbon byproduct or the hydrocarbon soot precursor violates a threshold, at least one of:
an operational status of the fibrous substrates of the respective pyrolysis reactor of the one or more pyrolysis reactors;
a maintenance action associated with a service life of the fibrous substrates of the respective pyrolysis reactor of the one or more pyrolysis reactors; or
a control action associated with one or more operating conditions of the respective pyrolysis reactor of the one or more pyrolysis reactors.

4. The system of claim 1, wherein the threshold represents an end-of-life of the one or more fibrous substrates, and further comprising a controller configured to output, in response to determining that the concentration of the at least one of the hydrocarbon byproduct or the hydrocarbon soot precursor violates the threshold, a maintenance indication.

5. The system of claim 1, further comprising a controller configured to initiate, in response to determining that the concentration of the at least one of the hydrocarbon byproduct or the hydrocarbon soot precursor violates the threshold, a shutdown of the respective pyrolysis reactor of the one or more pyrolysis reactors.

6. The system of claim 1, further comprising a controller configured to change a temperature profile along an axis of the respective pyrolysis reactor of the one or more pyrolysis reactors based on the concentration of the at least one of the hydrocarbon byproduct or the hydrocarbon soot precursor.

7. The system of claim 1, further comprising a controller configured to change a flow rate of the hydrocarbon into the respective pyrolysis reactor of the one or more pyrolysis reactors based on the concentration of the at least one of the hydrocarbon byproduct or the hydrocarbon soot precursor.

8. The system of claim 1, wherein the one or more pyrolysis reactors comprise a first pyrolysis reactor that includes a first concentration sensor and a second pyrolysis reactor that includes a second concentration sensor, wherein the first and second pyrolysis reactors are coupled in parallel.

9. The system of claim 8, further comprising a controller configured to:
receive, from the first concentration sensor, a measurement of the concentration of the at least one of the hydrocarbon byproduct or the hydrocarbon soot precursor from the first pyrolysis reactor; and
initiate, in response to determining that the concentration of the one or more hydrocarbon byproducts or soot precursors violates a threshold, a shutdown of the first pyrolysis reactor.

10. The system of claim 1, wherein each fibrous substrate of the one or more fibrous substrates has an effective void fraction between 40% and 95%.

11. A method for generating hydrogen gas, comprising:
pyrolyzing, by one or more pyrolysis reactors, a hydrocarbon to generate the hydrogen gas and carbon, wherein each pyrolysis reactor of the one or more pyrolysis reactors comprises one or more fibrous substrates defining a deposition surface for the carbon generated from the pyrolysis of the hydrocarbon, and wherein each fibrous substrate of the one or more fibrous substrates comprises a plurality of fibers configured to maintain chemical and structural stability between about 850° C. and about 1300° C.
measuring, by a concentration sensor downstream of at least one fibrous substrate of the one or more fibrous substrates, a concentration of at least one of a hydrocarbon byproduct or a hydrocarbon soot precursor.

12. The method of claim 11, wherein the at least one of the hydrocarbon byproduct or the hydrocarbon soot precursor measured by the concentration sensor comprises at least one of acetylene or benzene.

13. The method of claim 11, further comprising:
receiving, by a controller and from the concentration sensor, a measurement of the concentration of the at least one of the hydrocarbon byproduct or the hydrocarbon soot precursor; and
outputting, by the controller and in response to determining that the concentration of the at least one of the hydrocarbon byproduct or the hydrocarbon soot precursor violates a threshold, at least one of:
an operational status of the fibrous substrates of the respective pyrolysis reactor;
a maintenance action associated with a service life of the fibrous substrates of the respective pyrolysis reactor; or
a control action associated with one or more operating conditions of the respective pyrolysis reactor.

14. The method of claim 11, wherein the threshold represents an end-of-life of the one or more fibrous substrates, and wherein the method further comprises outputting, by a controller and in response to determining that the concentration of the at least one of the hydrocarbon byproduct or the hydrocarbon soot precursor violates the threshold, a maintenance indication.

15. The method of claim 11, further comprising initiating, by a controller and in response to determining that the concentration of the at least one of the hydrocarbon byproduct or the hydrocarbon soot precursor violates the threshold, a shutdown of the pyrolysis reactor.

16. The method of claim 11, further comprising changing, by a controller, a temperature profile along an axis of the pyrolysis reactor based on the concentration of the at least one of the hydrocarbon byproduct or the hydrocarbon soot precursor.

17. The method of claim 11, further comprising changing, by a controller, a flow rate of the hydrocarbon into the pyrolysis reactor based on the concentration of the at least one of the hydrocarbon byproduct or the hydrocarbon soot precursor.

18. The method of claim 11, wherein the one or more pyrolysis reactors comprise a first pyrolysis reactor that includes a first concentration sensor and a second pyrolysis reactor that includes a second concentration sensor, wherein the first and second pyrolysis reactors are coupled in parallel.

19. The method of claim 18, further comprising:
receiving, by a controller and from the first concentration sensor, a measurement of the concentration of the at least one of the hydrocarbon byproduct or the hydrocarbon soot precursor from the first pyrolysis reactor;
initiating, by the controller and in response to determining that the concentration of the at least one of the hydrocarbon byproduct or the hydrocarbon soot precursor violates the threshold, a shutdown of the first pyrolysis reactor.

20. The method of claim 11, wherein each fibrous substrate of the one or more fibrous substrates has an effective void fraction between 40% and 95%.

* * * * *